(12) United States Patent
Narasimharao et al.

(10) Patent No.: US 10,987,657 B1
(45) Date of Patent: Apr. 27, 2021

(54) GOLD SUPPORTED YTTRIUM OXIDE NANORODS AND METHODS OF USE THEREOF

(71) Applicant: King Abdulaziz University, Jeddah (SA)

(72) Inventors: Katabathini Narasimharao, Jeddah (SA); Abdulmohsen Ali Alshehri, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/029,227

(22) Filed: Sep. 23, 2020

(51) Int. Cl.
| | |
|---|---|
| *B01J 23/52* | (2006.01) |
| *B01J 23/10* | (2006.01) |
| *C07C 4/06* | (2006.01) |
| *C07C 5/32* | (2006.01) |
| *B01J 35/00* | (2006.01) |
| *B01J 35/08* | (2006.01) |

(52) U.S. Cl.
CPC .............. *B01J 23/52* (2013.01); *B01J 23/10* (2013.01); *B01J 35/0013* (2013.01); *B01J 35/08* (2013.01); *C07C 4/06* (2013.01); *C07C 5/324* (2013.01); *C07C 2523/10* (2013.01); *C07C 2523/52* (2013.01)

(58) Field of Classification Search
None
See application file for complete search history.

(56) References Cited

U.S. PATENT DOCUMENTS

| | | | |
|---|---|---|---|
| 2011/0129537 A1 | 6/2011 | Vo-Dinh et al. | |
| 2014/0274671 A1 | 9/2014 | Schammel et al. | |

FOREIGN PATENT DOCUMENTS

CN    106000400 A  *  10/2016  .............. B01J 23/63

OTHER PUBLICATIONS

Machine translation CN 106000400. Published Oct. 12, 2016, Retrieved Dec. 30, 2020. (Year: 2020).*
Li et al. "Fabrication of Ag/La(OH)3 Nanorod Framework Composites Through Dealloying for CO Oxidation" Journal of the Minerals Metals & Materials Society 71, 522-530 (2019). (Year: 2019).*
Boyadjian et al., "Catalytic Oxidative Cracking of Light Alkanes to Alkenes", EurJIC, Mar. 5, 2018.
Emayavaramban et al. "Gold Nanoparticles Supported on Magnesium Oxide Nanorods for Oxidation of Alcohols", Journal of Nanoscience and Nanotechnology, vol. 16, 2517-2526, Mar. 2016.
Guzman et al., "Nanocrystalline and mesostructured Y2(O3) as supports for gold catalysts", Chem Commun, Feb. 14, 2005; (6):743-5.

(Continued)

*Primary Examiner* — Philip Y Louie
*Assistant Examiner* — Alyssa L Cepluch
(74) *Attorney, Agent, or Firm* — W & C IP

(57) ABSTRACT

A catalyst comprising $Y_2O_3$ nanorods and gold nanoparticles dispersed on a surface of the nanorods is provided. The gold is present at a concentration of 0.5-2 wt %. A method of forming olefins by oxidative cracking is also provided. The method includes reacting an alkane with a reactant gas mixture in the presence of a catalyst under conditions suitable for forming light olefins (ethtylene and propylene).

13 Claims, 10 Drawing Sheets
(3 of 10 Drawing Sheet(s) Filed in Color)

(56) References Cited

OTHER PUBLICATIONS

Narasimharao et al., "Catalytic Oxidative Cracking of Propane Over Nanosized Gold Supported Ce0.5Zr0.5O2 Catalysts", Catal Lett (Jul. 20, 2013) 143:1074-1084.

Sreethawong et al., "Preparation of Au/Y2O3 and Au/NiO catalysts by co-precipitation and their oxidation activities", Materials Chemistry and Physics 126 (2011) 212-219.

* cited by examiner

GOLD SUPPORTED YTTRIUM OXIDE NANORODS AND METHODS OF USE THEREOF

FIELD OF THE INVENTION

The invention is generally related to gold supported $Y_2O_3$ nanorods that may be utilized as catalysts for oxidative cracking of alkanes to produce olefins.

BACKGROUND OF THE INVENTION

Production of new synthetic materials is still growing due to rapidly developing world demands for advanced materials to improve the quality of life [1]. The demand for petrochemical raw materials such as light olefins (ethene, propene and butene) is increasing enormously, as the present industrial production of light olefins is not sufficient [2]. Conventionally, the petrochemical industries are producing the light olefins by catalytic or steam cracking of naphtha or natural gas and also using fluid catalytic cracking of vacuum residue oil [3]. Although, these two processes are well studied and commercialized, there are several disadvantages in the two processes [4]. As strong environmental regulations were placed across the world, there are limits to the use of byproducts (aromatics) in the fuel and petrochemical refineries are unable to catch up with the industry needs pertaining to olefin production processes [5].

On-purpose propene production processes such as methanol-to-olefins [6], metathesis of ethylene and butylene [7], dehydrogenation of n-propane [8] and catalytic oxychlorination of n-propane to propene [9, 10] have been developed due to high demand of propene and the exhaustion of natural petroleum resources. Among the studied processes, dehydrogenation of alkanes is a simple process, however it suffers from several disadvantages such as its endothermic nature, high coke deposition and short catalyst lifetime [11]. Later, researchers developed a catalytic oxidative dehydrogenation process to overcome the disadvantages of the dehydrogenation process [12, 13]. Although many research efforts were dedicated to development, industrial application of the oxidative dehydrogenation process has not been materialized due to the low olefin selectivity [14]. Recently, a catalytic oxidative cracking process was recognized as a prospective alternative route to existing processes [15]. This is primarily due to the fact that this process carries several advantages such as an exothermic nature, which diminishes external heat input and lowers capital costs, presence of oxygen in the reactant feed assists to minimize the coke formation and the utilization of an effective catalyst could activate the reacting molecules at lower reaction temperatures, allowing to improve the selectivity of light olefins [16].

Several supported vanadium oxide catalysts were utilized for cracking of hydrocarbons due to redox properties of the mixed transition metal oxides [17]. However, many investigated mixed oxide catalysts were not capable due to re-adsorption of light olefins resulting in complete oxidation to $CO_x$ (olefin yields below 30%) [18]. Landau et al [19] used MgO supported rare-earth oxides and alkali chloride promoted catalysts and observed enhanced olefin yield up to 55%. Previously, several acidic (protonic form of MFI zeolites), basic (mixed alkaline earth metal oxides) and pure transition metal oxide catalysts were utilized for oxidative cracking of alkanes [20]. Recently, it was also observed that $Ce_{0.5}Zr_{0.5}O_2$, $Y_2O_3$ and $La_2O_3$ based catalysts possessed considerable activity for oxidative cracking of n-propane [21]. Many researchers devoted to study the gold supported catalysts due to superior performance of nanosized gold for oxidation reaction [22]. It was later reported that highly dispersed nanosized gold particles on metal oxide supports could offer exceptional catalytic activity at low reaction temperatures [23]. Further it was observed that morphology, size of gold particles and also the type of support influences the catalyst performance in oxidation reactions [24]. It was observed that the acidity of the support affects the propene selectivity because of the interferences in the catalytic cracking and alkene oligomerization [25]. It was also reported that weak metal-support interaction generally lead to the aggregation of metal species, which could result in pore blockage and coke formation. Therefore, for selective propene production, it is essential that the support should possess minimum acidity and be able to interact with active metal species.

SUMMARY

Described herein are gold supported yttrium oxide ($Y_2O_3$) nanorods (NR) that may be utilized as catalysts for oxidative cracking of alkanes to produce olefins. There is a synergistic effect between the gold and $Y_2O_3$—NR support due to strong metal-support interaction. Gold deposition results in an increase in the number of mobile oxygen species and Lewis acidic sites. Time on stream analysis indicates that gold supported $Y_2O_3$ nanorod catalysts exhibited considerable stable activity for 24 h. Further, the catalysts have a high selectivity towards to propylene production, which is commercially valuable.

An aspect of the disclosure provides a catalyst comprising $Y_2O_3$ nanorods and gold nanoparticles dispersed on a surface of the nanorods, wherein the gold is present at a concentration of 0.5-2 wt %. In some embodiments, the $Y_2O_3$ nanorods have a diameter ranging from 10-20 nm. In some embodiments, the $Y_2O_3$ nanorods have a length ranging from 75-110 nm. In some embodiments, the gold nanoparticles are spherical in shape. In some embodiments, the gold nanoparticles have a diameter ranging from 20-50 nm.

Another aspect of the disclosure provides a method of forming olefins by oxidative cracking comprising reacting an alkane with a reactant gas mixture in the presence of a catalyst as described herein under conditions suitable for forming olefins. In some embodiments, the alkane is n-propane and the olefins comprise ethylene and propylene. In some embodiments, the reactant gas mixture comprises oxygen and argon. In some embodiments, the reactant gas mixture comprises 15-25% oxygen and 75-85% argon. In some embodiments, the reaction is performed at a temperature of 450° C. to 650° C. In some embodiments, the reaction occurs under a gas hourly space velocity (GHSV) of 47000-49000 $h^{-1}$. In some embodiments, at least 75% of the alkane is converted in the reaction. In some embodiments, the reaction has olefins selectivity of at least 90%.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
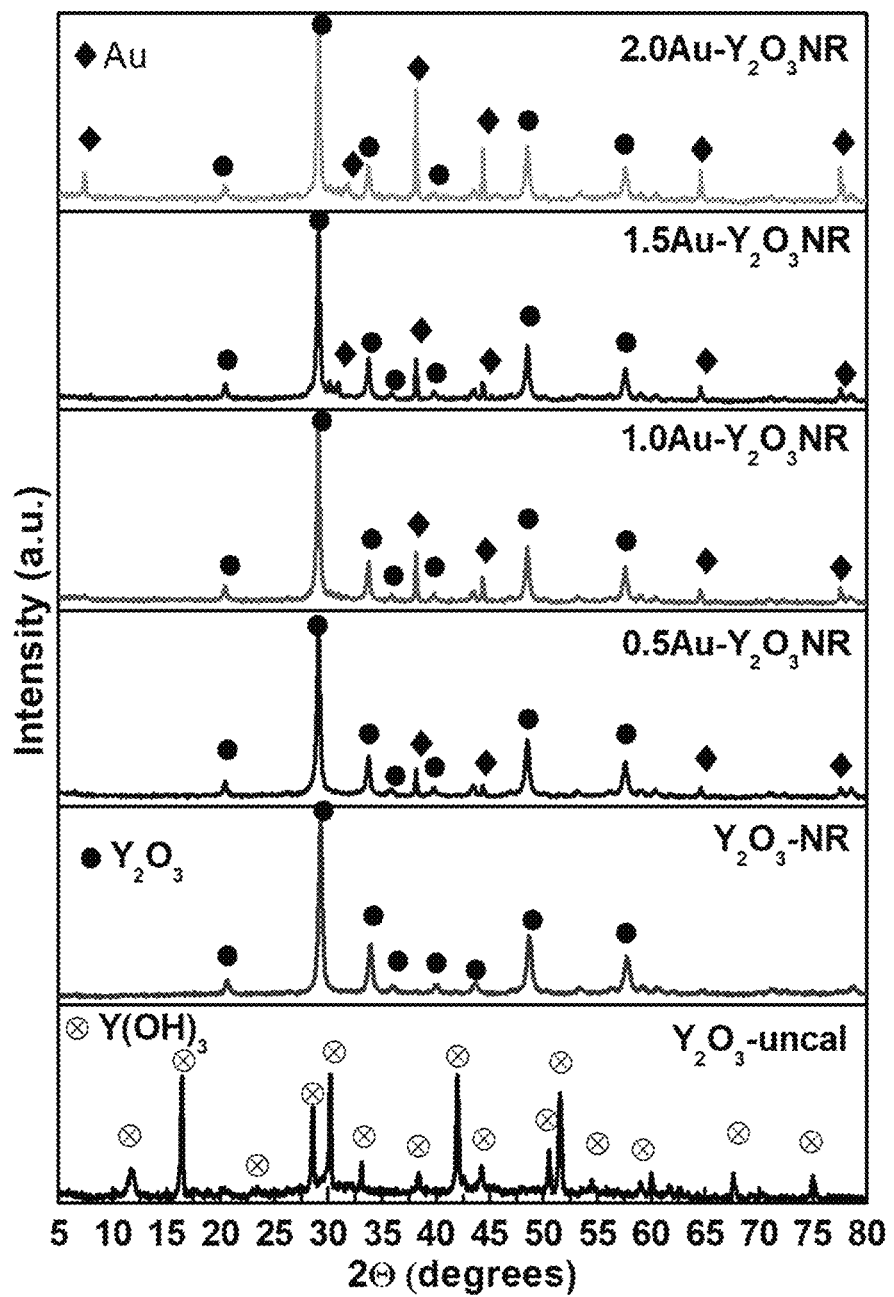
FIG. 1. XRD patterns of gold supported $Y_2O_3$ nanorods.

Embodiments of the disclosure provide gold supported yttrium oxide (Y$_2$O$_3$) nanorods that may be utilized as catalysts for oxidative cracking of alkanes such as n-propane to produce light olefins such as ethylene and propylene. Gold deposition provides a significant enhancement in both alkane conversion and olefins selectivity. This synergistic effect between the gold and Y$_2$O$_3$ nanorod support is due to a strong metal-support interaction.

As used herein, "nanorods" are rod-shaped particles that have a length at least twice a radius or width and are typically 1 to 200 nm in length. The nanorods are solid structures composed, at least partially, of the metal oxide. The nanorods are single crystals.

Y$_2$O$_3$ has been utilized as a catalyst or catalytic support in different reactions due to its basic nature. It was also found that Y$_2$O$_3$ is a suitable catalyst for oxygen activation [26], in addition it possesses excellent hydrothermal stability [27]. As described herein, Y$_2$O$_3$ is utilized to be a support to disperse gold nanoparticles. Yttrium oxide nanorods may be synthesized by methods known in the art e.g. by an alkali assisted hydrothermal synthesis method. For example, crystalline yttrium nitrate may be dissolved in double distilled water. To this solution, potassium hydroxide solution may be added under constant stirring to obtain a precipitate having a pH around 13. Then, the obtained precipitate subjected to a hydrothermal treatment, and subsequently cooled to obtain a white colored solid product. After washing, the cake is dried and then calcined to obtain yttrium oxide nanorods.

Other methods for producing nanorods include, for example, controlled vapor-solid growth processes using a metal vapor source.

The yttrium oxide nanorods may be loaded with gold nanoparticles using, for example, a chemical reduction method. For example, after dissolution of a gold precursor (e.g. HAuCl$_4$) in water, an appropriate amount of a reducing agent (e.g. NaBH$_4$) is added to reduce the Au precursor and produce gold nanoparticles. The Y$_2$O$_3$ nanorods are impregnated with the gold nanoparticles, washed, dried, then calcined to provide gold nanoparticles dispersed on the surface of Y$_2$O$_3$ nanorods.

In some embodiments, the gold is present at a concentration of 0.5-2 wt %, e.g. about 1.5% based on the weight of the total catalyst including the nanorods. In some embodiments, the Y$_2$O$_3$ nanorods have a diameter ranging from 10-20 nm, e.g. about 15 nm. In some embodiments, the Y$_2$O$_3$ nanorods have a length ranging from 75-110 nm. In some embodiments, the gold nanoparticles are spherical in shape. In some embodiments, the gold nanoparticles have a diameter ranging from 20-50 nm.

Further embodiments provide a method of forming olefins by oxidative cracking comprising reacting an alkane with a reactant gas mixture in the presence of a catalyst as described herein under conditions suitable for forming olefins. In some embodiments, the alkane is n-propane. Other suitable alkanes include, but are not limited to, ethane and n-butane. Suitable olefins include, but are not limited to, ethylene, propylene, and butylene.

The amount of catalyst added to the reaction is a catalytically effective amount. As used herein, the term "catalytically effective amount" refers to an amount of catalyst that provides a measurable conversion of alkane to olefins. The exact concentrations employed, of course, will depend on, among other factors, the desired catalytic properties. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity. It may be desirable to intentionally change the operating conditions to take advantage of certain catalytic properties even at the expense of other catalytic properties. The exact operating conditions will depend upon, among other factors, feedstock costs, energy costs, by-product removal costs and the like.

The conditions for carrying out an oxidative cracking reaction in the presence of the catalyst of the present disclosure broadly comprise those described in the prior art. This applies, for example, to suitable temperatures, pressures, residence times, diluent materials, the presence or absence of moderating agents to control the catalytic action, the desirability of employing recycle operations or applying successive conversion in different reactors to increase the yields of olefins, and any other special conditions which may be selected in processes for preparing olefins.

In some embodiments, the reactant gas mixture comprises oxygen and argon. In some embodiments, the reactant gas mixture comprises 15-25%, e.g. about 20% oxygen and 75-85%, e.g. about 80% argon. In some embodiments, the reaction is performed at a temperature of 450° C. to 650° C., e.g. about 600° C. In some embodiments, the reaction occurs under a gas hourly space velocity (GHSV) of 47000-49000 h$^{-1}$, e.g. about 48000 h$^{-1}$. GHSV is the volume of gaseous reactant mixture, measured at 0° C. and 1 atm pressure, passed through a unit volume of reactor per hour.

Total conversion of reactant (%)=percent of the reactant converted to all the products. Conversion of a reactant to a particular product=percent of the reactant converted to the particular product. In some embodiments, at least 75%, e.g. at least 80%, 85%, 90%, 95% or more, of the alkane is converted in the reaction.

Selectivity for a particular product (%)=100×[Conversion of reactant to the product (%)]/[Total conversion of reactant (%)]. In some embodiments, the reaction has a selectivity of at least 90%, e.g. at least 91%, 92%, 93%, 94%, 95%, 96%, 97%, 98%, 99%, or more.

All the ratios of reactants or products described herein are mole ratios.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

An alkali assisted hydrothermal method was utilized to synthesize $Y_2O_3$ nanorods. Gold (0.5, 1.0, 1.5 and 2.0 wt. %) supported $Y_2O_3$ nanorods samples were prepared by chemical reduction method and the synthesized Au—$Y_2O_3$ nanomaterials were utilized as catalysts for oxidative cracking of n-propane. The bulk $Y_2O_3$ nanorods showed n-propane conversion of 20% with 25% light olefins (ethylene and propylene) selectivity at 600° C. Significant enhancement in both n-propane conversion and olefins selectivity were observed after gold deposition. Gold (1.5 wt. %) supported $Y_2O_3$ nanorods (1.5Au—$Y_2O_3$—NR) sample offered highest activity (75.5% conversion of n-propane and 90.3% olefins selectivity) at 600° C. Different techniques such as elemental analysis, powder X-ray diffraction, FT-IR, FE-SEM, DR UV-vis, $N_2$-physisorption, XPS and $H_2$-TPR measurements were used to determine physico-chemical properties of the synthesized catalysts. The characterization results revealed an existence of synergistic effect between the gold and $Y_2O_3$—NR support due to strong metal-support interaction. The superior catalytic activity of 1.5Au—$Y_2O_3$—NR sample is due to the fact that this catalyst possessed more number of mobile oxygen species, large number of Lewis acidic sites and also $Au^{\delta+}$—O—Y species. Time on stream analysis indicated that gold supported $Y_2O_3$ nanorod catalysts exhibited considerable stable activity for 24 h with slight loss of performance due to agglomeration of gold particles.

Materials and Methods

Synthesis of Catalysts

Yttrium oxide nanorods: Yttrium oxide nanorods were synthesized by adapting alkali assisted hydrothermal synthesis method. In a typical synthesis, 7.66 g of crystalline yttrium nitrate was dissolved in 100 mL of double distilled water. To this solution, 2.0 M potassium hydroxide solution was added dropwise under constant stirring to obtain a precipitate (pH is around 13). Then, the obtained precipitate was transferred into a Teflon lined stainless steel vessel and it was heated at 160° C. for 48 h. After the hydrothermal treatment, the vessel was brought to 25° C. and the obtained white colored solid product was collected and washed with distilled water for five times and finally with diluted HCl to remove any remained KOH. The washed cake was first dried in an oven over for 120° C. for 24 h and then material was calcined at 650° C. for 6 h in air to obtain the yttrium oxide nanorods. The calcined product was labelled as $Y_2O_3$—NR.

Gold supported yttrium oxide nanorods: Gold (0.5, 1.0, 1.5 and 2.0 wt %) supported $Y_2O_3$—NR catalysts were prepared by simple chemical reduction method. The calculated amount of $HAuCl_4$ corresponding to gold loading was dissolved in 50 mL of double distilled water. After complete dissolution of Au precursor, an appropriate amount of aqueous 0.1 M $NaBH_4$ solution (molar ratio of $NaBH_4$/Au=10) was added to reduce the Au precursor and the resulting nanoparticles are kept under stirring for 30 minutes. Then, calculated amount of $Y_2O_3$—NR to obtain 0.5, 1.0, 1.5 and 2.0 wt % of Au in the final samples. The excess water was separated by centrifugation and the residual solid product was washed with distilled water for five times, then the material was dried at 110° C. for 12 hours. Finally, the dried materials were calcined at 300° C. for 4 hours in an electric furnace.

Characterization of Synthesized Materials

The elemental composition of the synthesized materials was determined by using ICP-AES, Optima 7300DV (Perkin-Elmer) instrument. The XRD patterns of the powders were collected by using PANalytical XpertPro diffractometer. The crystallite size of obtained materials was determined by applying the Debye-Scherer equation The SEM analysis of the samples was carried out using JEOL Model JSM-6390LV microscope. The FT-IR spectra of calcined materials were obtained using Bruker vertex 70 FT-IR spectrometer. The acidic character of the samples was investigated by pyridine adsorption measurements using FT-IR spectroscopy; the analysis was performed over calculated amount of catalyst, which was treated at 100° C. under vacuum for 5 h. Then, the sample was treated with pyridine vapor and finally heated at 100° C. under vacuum for 30 min to remove physically adsorbed pyridine [30]. FT-IR spectra were collected at room temperature. XPS spectra of the materials were collected by using Kratos Axis Nova spectrometer. The textural properties of the samples were obtained from the $N_2$-physisorption experiments, which were conducted using Quantachrome ASiQ adsorption system. The $H_2$-TPR and $O_2$-TPD experiments were performed by using Quantachrome CHEMBET-3000 system. For the $O_2$-TPD experiments, a known amount catalyst was first pretreated in helium gas flow at 120° C. for 2 h. After the temperature of the sample cooling to 25° C., the sample was exposed to $O_2$ gas for 1 h and then flushed the sample with helium gas [31]. Finally, the $O_2$-TPD patterns were obtained by heating the sample to 700° C., with a heating rate of 10° C. $min^{-1}$. The dispersion of the gold nanoparticles over the $Y_2O_3$—NR support was determined by using CO pulse chemisorption measurements. Prior to analysis, known amount of the sample (100 mg) was reduced at 350° C. under $H_2$ flow (40 mL $min^{-1}$) for 60 min and then cooled to 25° C. under the flow of helium gas. Then, the CO pulse injection was conducted in a flow of helium gas stream. The gold dispersion was evaluated from the amount of CO consumption (assuming CO/Au=1).

Catalytic Oxidative Cracking of n-Propane

Oxidative cracking of n-propane measurements over synthesized catalysts were performed using a fixed bed quartz reactor. The reactor was loaded with weighed catalyst pellets (200 mg), which were diluted with unreactive quartz particles. The reactant gas mixture, which contained n-propane (20 mL $min^{-1}$), 20% oxygen-80% argon (100 mL $min^{-1}$) and argon (40 mL $min^{-1}$) was used to perform the catalytic tests. Different reaction temperatures were used to investigate the effect of reaction temperature on the catalyst performance. The composition of product gas mixture was continuously analyzed with assistance of Agilent 6890 A gas chromatograph equipped with flame ionization and thermal conductivity detectors.

Results and Discussion

Powder X-ray diffraction (XRD) patterns of synthesized gold supported $Y_2O_3$ nanorod samples and uncalcined $Y_2O_3$ sample are shown in FIG. 1. The uncalcined $Y_2O_3$ sample exhibited major reflections at 2θ=16.4°, 28.5°, 30.2°, 38°, 42.2°, 50.1°, 51.4° which could be attributed to the crystal planes of (100), (110), (101), (111), (201), (300), (211) of hexagonal $Y(OH)_3$ phase [JCPDS file No. 24-1422]. After calcination at 650° C., the sample exhibited reflections at 2θ=20.6°, 29.3°, 33.9°, 48.5°, and 57.6° which could be attributed to (211), (222), (400), (440) and (622) planes of cubic $Y_2O_3$ phase [JCPDS card No. 25-1200]. This observation clearly indicating the formation of single-phase $Y_2O_3$ phase after thermal treatment at 650° C. The Au supported $Y_2O_3$—NR samples showed reflections at 2θ=38.2°, 44.2°, 64.4° and 77.6° due to (111), (200), (220) and (311) planes of face centered cubic structure of Au metal particles [JCPDS file No. 04-0784]. The presence of intense reflection at 38.2° in all the XRD patterns indicating that the Au metal particles were growth in (111) direction. The intensity of the reflections due to Au metal particles were found to increase with increase of Au loading which revealing the enhancement in crystallinity of Au particles. These observations are revealing that formation of pure Au metal nanocrystals in the Au supported $Y_2O_3$ samples.

The average crystallite sizes of $Y_2O_3$ nanotubes [intense reflection due to (222) plane] and Au particles [intense reflection due to (111) plane] were calculated using Scherer's formula. The Au metal particle size was observed as 12.3 nm, 18.5 nm, 30.2 nm and 47.5 nm for samples with Au loading of 0.5, 1.0, 1.5 and 2.0 wt % respectively. It is observed that the crystallite size of $Y_2O_3$ phase (15 nm) have not changed considerably with increase of Au loading.

Figure 2:
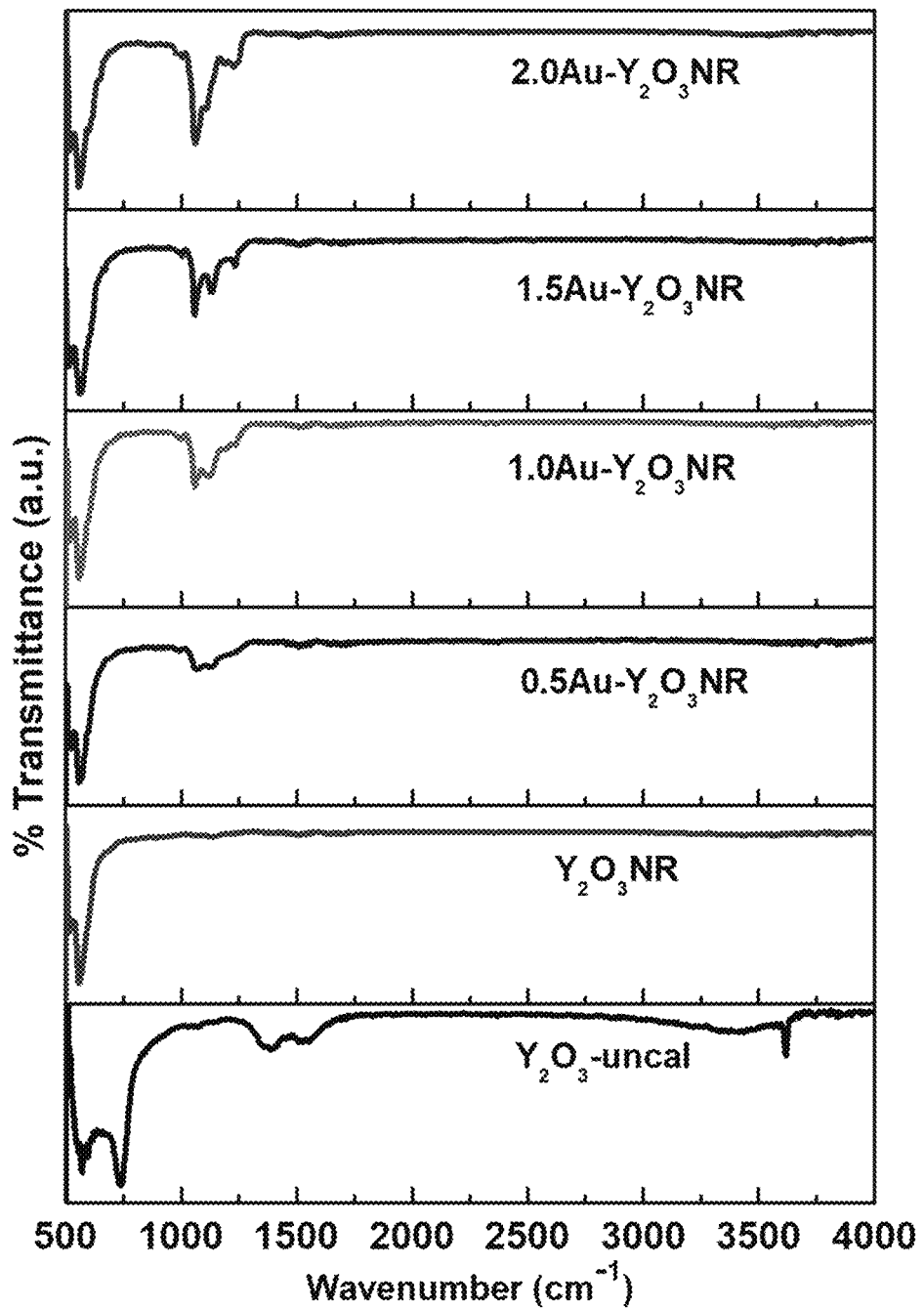
FIG. 2. FT-IR spectra of gold supported $Y_2O_3$ nanorods.
Figure 3A:
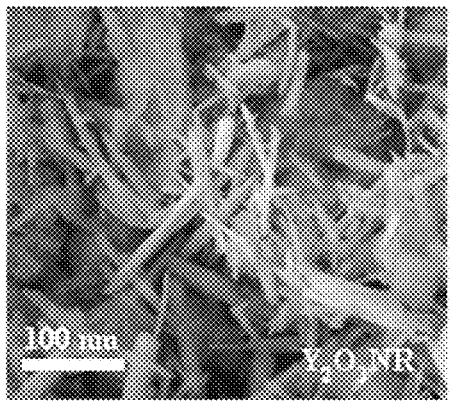
FIGS. 3A-E. FE-SEM images of gold supported $Y_2O_3$—NR samples: (A) $Y_2O_3$ nanorods, (B) 0.5Au—$Y_2O_3$ nanorods, (C) 1.0Au—Y$_2$O$_3$ nanorods, (D) 1.5Au—Y$_2$O$_3$ nanorods, and (E) 2.0Au—Y$_2$O$_3$ nanorods.
Figure 3B:
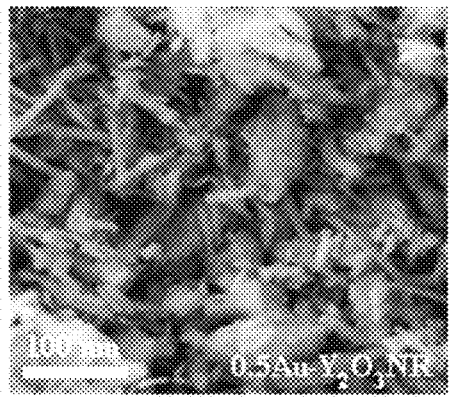
Figure 3C:
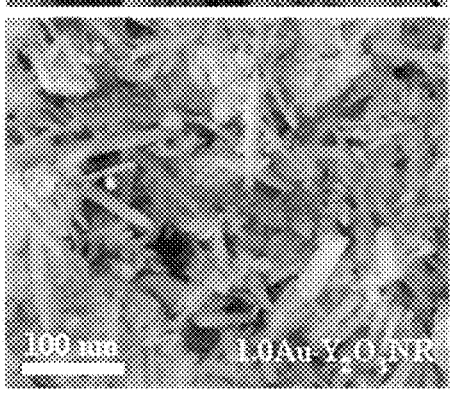
Figure 3D:
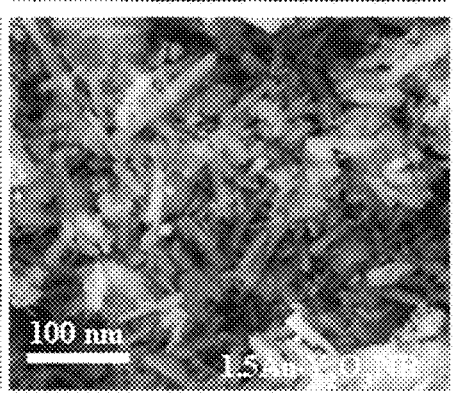
Figure 3E:
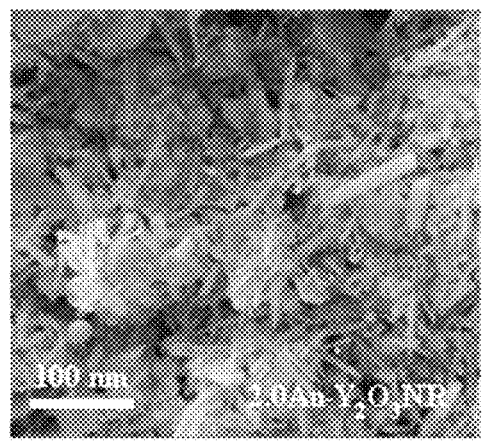

FIG. 2 displays the FT-IR spectra of uncalcined $Y_2O_3$ and gold supported $Y_2O_3$ nanorod samples calcined at 650° C. FT-IR spectrum of uncalcined $Y_2O_3$ sample showed a sharp band at 3645 $cm^{-1}$, which could be attributed to stretching vibration of —OH groups presented in the crystal lattice of $Y(OH)_3$ [32]. The broad bands at 1550 $cm^{-1}$ and 1385 $cm^{-1}$ could be assigned to symmetric and asymmetric stretching vibrations of C—O and N—O bonds in $[CO_3]^{2-}$ and $[NO_3]^{-}$ groups, respectively [33].

It was previously reported that these two bands appears due to the absorption of $CO_2$ on surface of $Y(OH)_3$ and presence of some unconverted hydroxynitrate [34]. The bands at 570 $cm^{-1}$ and 733 $cm^{-1}$ could be assigned to stretching vibrations of yttrium bonded with hydroxide and nitrate ions [35].

It is clear from the FTIR spectrum $Y_2O_3$—NR sample that after the thermal treatment at 650° C., the bands due to hydroxyls, carbonate and hydroxynitrate species disappeared and a new band appeared at 560 $cm^{-1}$, which could be assigned to the stretching vibration of Y—O bond of $Y_2O_3$ nanorods [36]. The FT-IR spectra of gold supported $Y_2O_3$—NR samples exhibited stretching vibration of Y—O bond along with multiple bands in the range of 1060-1230 $cm^{-1}$, which are related to different vibrations of carboxylate groups generated due to $CO_2$ absorption [37]. It is clear that the intensity of these bands increased with increase of gold loading from 0.5 to 2.0 wt. %, revealing more gold nanoparticles are available on the surface of the 2.0Au—$Y_2O_3$NR catalyst.

The morphology of the synthesized gold supported $Y_2O_3$—NR materials was investigated by FE-SEM analysis (FIG. 3A-E). The SEM image of $Y_2O_3$—NR sample clearly showed randomly distributed nanorods with 100-150 nm in length and 10 to 20 nm diameter. Deposition of gold particles resulted in a slight change in the morphology of the $Y_2O_3$ nanorods; the long rods were broken into short nanorods with average diameter of 15 nm and length of 75-110 nm. The short $Y_2O_3$ nanorods were appeared in all gold supported samples. The morphology difference in the pure $Y_2O_3$—NR and gold supported $Y_2O_3$—NR samples is probably due to the chemical reduction method used to prepare the gold nanoparticles. The images reveals the presence of closely packed nanorods with uneven morphology and also pores created due to the spaces existed due to packing of nanorods. The existence of near spherical gold nanoparticles with sizes in the range of 20-50 nm, are dispersed on the surface of $Y_2O_3$ nanorods are clearly visible in the SEM images of gold supported $Y_2O_3$—NR samples. The $Y_2O_3$—NR samples with high gold content exhibited the presence of accumulated secondary particles composed of non-uniform $Y_2O_3$ nanorods and gold nanoparticles, which could lead to wide-range particle size distribution.

Figure 4:
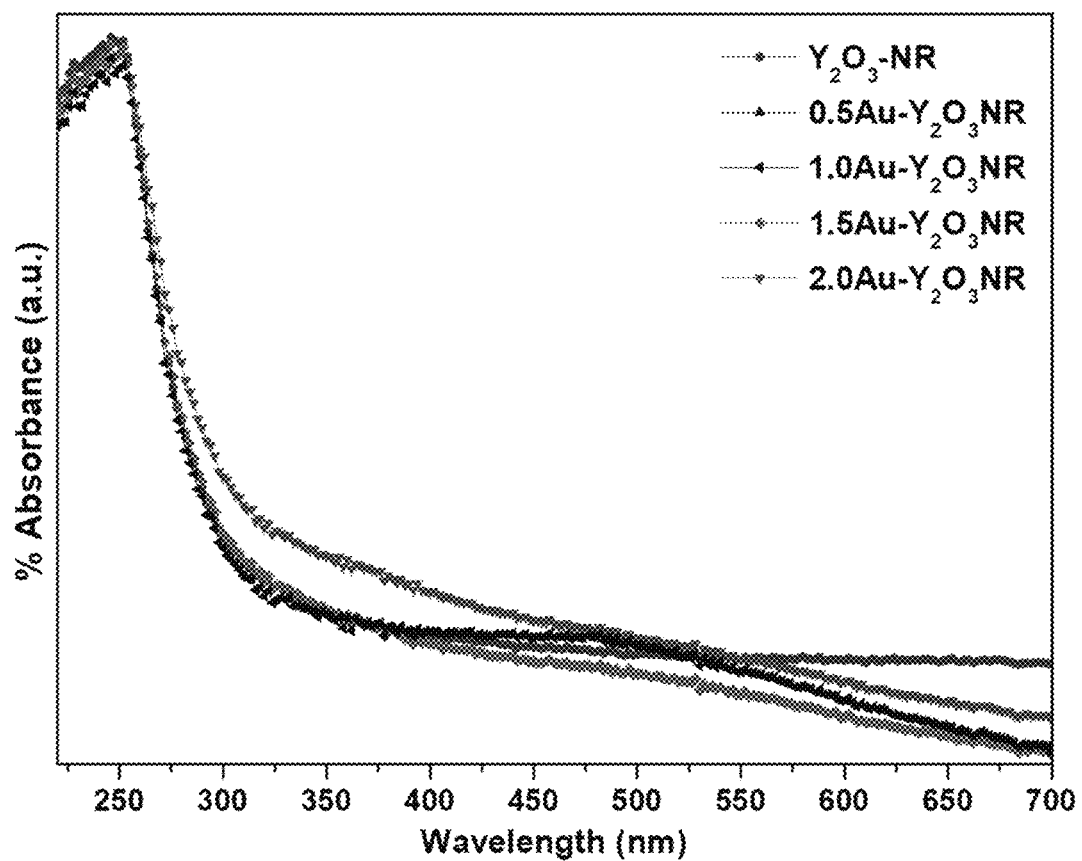
FIG. 4. DR UV-vis spectra of gold supported Y$_2$O$_3$—NR samples.

FIG. 4 displays DR UV-vis spectra of gold deposited $Y_2O_3$—NR samples. The $Y_2O_3$—NR sample exhibited sharp absorption band at 250 nm. Deposition of gold particles over $Y_2O_3$—NR have not modified this absorption band, despite the fact that the small size nanorods were formed due to breakage of long $Y_2O_3$ nanorods after gold deposition. Xu et al [38] observed that UV-vis spectrum of pure $Y_2O_3$ nanoparticles showed major absorption band at 250 nm, due to band gap of $Y_2O_3$. It is clear from the FIG. 4 that gold supported $Y_2O_3$—NR samples exhibited a broad absorption band centered at 500 nm. Previously, it was observed that the Surface Plasmon Resonance (SPR) peak for the gold nanoparticles generally appears at 510 nm and the intensity of this peak gradually improved with increase of gold loading. The presence of SPR band indicating that the samples clearly possessed gold metal nanoparticles [39].

The textural properties of gold supported $Y_2O_3$—NR samples are determined from $N_2$-physical adsorption experiments. The materials showed Type-III isotherms as per IUPAC classification and it is clear that isotherms have not shown any curvature at lower pressures [40]. This observation indicating that the materials possessed either macro pores or no pores at all, as a weak nitrogen-material interaction is clearly evident. It is also clear that the isotherms exhibited Type H3 hysteresis loop, which is an indication that aggregated particles of the materials were arranged randomly to form macro size pores [40]. To get detailed information of the pore structure of the samples, the pore size distribution patterns were obtained. The synthesized materials exhibited meso and macro pores. The intensity of the pore size distribution peaks were decreased in case of gold deposited $Y_2O_3$—NR samples. This is probably due to the deposition of gold nanoparticles on the surface as well as inside of the $Y_2O_3$ agglomerates. The BET surface area, pore volume and pore diameter of the synthesized materials are shown in Table 1. The results clearly indicate that the BET surface area and pore volume of materials were decreased gradually with increase of gold loading from 0.5 wt % to 2.0 wt %. The bulk $Y_2O_3$ NR sample calcined at 650° C. exhibited surface area of 59 $m^2g^{-1}$ and pore volume of 0.142 $cm^3g^{-1}$, after 2.0 wt % gold deposition, the surface area and pore volume decreased to 39 $m^2g^{-1}$ and pore volume of 0.127 $cm^3g^{-1}$ respectively. However, it is interesting to note that the average pore diameter of the samples has not changed significantly. The bulk $Y_2O_3$—NR sample possessed a pore size of 15.4 nm, while it was decreased to only 14.4 nm after 2.0 wt % gold deposition. This is possibly due to the fact that the deposited gold nanoparticles are partially blocking pores of $Y_2O_3$ nanorods, which resulted in a decline in surface area and pore volume. The reason for the slight change in the average pore diameter is that the majority of the pores are formed due to the presence of large voids among the $Y_2O_3$ nanorods and they were not blocked by the gold particles. These observations are corroborated with results obtained in SEM analysis of the samples.

TABLE 1

Elemental composition and textural properties of gold supported $Y_2O_3$ nanorods.

| | Bulk elemental analysis (ICP-AES) (wt. %) | | | Surface elemental analysis (XPS) (wt. %) | | | Textural properties | | |
|---|---|---|---|---|---|---|---|---|---|
| Sample | Au | Y | O | Au | Y | O | Surface area ($m^2g^{-1}$) | Pore volume ($cc\ g^{-1}$) | Pore diameter (nm) |
| $Y_2O_3$NR | — | 85.2 | 14.8 | — | 84.9 | 15.1 | 65 | 0.142 | 15.4 |
| 0.5Au—$Y_2O_3$NR | 0.43 | 84.1 | 15.4 | 0.38 | 83.8 | 15.8 | 48 | 0.140 | 14.5 |
| 1.0Au—$Y_2O_3$NR | 0.68 | 81.2 | 18.1 | 0.53 | 80.8 | 18.6 | 34 | 0.136 | 14.5 |
| 1.5Au—$Y_2O_3$NR | 1.27 | 79.7 | 19.0 | 1.14 | 79.0 | 19.8 | 22 | 0.131 | 14.4 |
| 2.0Au—$Y_2O_3$NR | 1.70 | 78.3 | 20.0 | 1.36 | 77.5 | 21.1 | 14 | 0.127 | 14.4 |

The surface properties such as composition and electronic states of elements in the synthesised samples was studied by means of XPS analysis (data not shown). The Y 3d XP spectra for bulk $Y_2O_3$—NR sample exhibited two contributions at 157 eV ($3d_{5/2}$) and 159 eV ($3d_{3/2}$). It was reported that bulk $Y_2O_3$ sample showed the XP peak at 156.8 eV ($3d_{5/2}$) and the fitted Y3d spectrum showed a doublet with a separation binding energy of 2.06 eV [41]. The shape and positions of the Y3d peak observed in the samples are in accordance with reported observations in the literature. The Y3d spectra for gold deposited samples also has been fitted with two peaks at 156 eV and 158 eV and these peaks are at lower binding energy compared to bulk $Y_2O_3$—NR sample. It was previously reported that presence of highly electronegative ions such as $CO_3^{2-}$ and $(OH)CO_3^-$ could result an increase of binding energy values of Y species [42]. However, peaks are shifted to lower values in spectra for gold supported samples. The peak shift may therefore be due to presence of Y—O—$Au^+$ or Y—O—$Au^{3+}$ species resulting shift in binding energy to lower values.

It was previously reported that the variations in the chemical state or structural aspects of the Au surface could be studied by comparing the core-level shifts in the Au4f spectra of the samples [43] It is clear from the XPS analysis that the gold deposited samples showed clear Au4f XP peaks attributed to $Au4f_{7/2}$ and $Au4f_{5/2}$ contributions. It was reported that the $4f_{7/2}$ binding energy values for $Au^0$, $Au^+$ and $Au^{3+}$ oxidation states are 84.0 eV, 85.5 eV and 86.4 eV respectively [44]. Deconvolution of core-level Au 4f spectrum of 1.0Au—$Y_2O_3$—NR sample showed a small tail peak at 83.0 eV and major peak at 86.2 eV; indicating that this sample majorly contained surface $Au^{3+}$ species with minor $Au^0$ species. The binding energy of the $Au4f_{7/2}$ peak is shifted to 85 eV (lower value) as gold loading raised to 1.5 wt %. Increase of gold deposition to 2.0 wt % resulted lowering of binding energy further for $Au4f_{7/2}$ peak to 84.3 eV. It is clear that the binding energy of the tail peak have not changed considerably and the intensity of this peak increased gradually with increase of gold loading. These observations are indicating that the amount of surface $Au^0$ species were increased with increase of gold loading, as the nature of gold-support interactive species also changed. Therefore, it is possible to argue that the oxidized Au species ($Au^{\delta+}$) might have electronic state between +1 and +3. A similar observation reported in the literature that the Au nanoparticles could anchor with defective sites of metal oxide support [45]. The XRD patterns and DR UV-vis spectra of the materials clearly revealed the presence of $Au^0$ species and the amount of these species increased with increase of gold loading. Interestingly, the XPS spectra of samples revealed the presence of more oxidized Au species than metallic Au species on surface of the catalysts. This is possibly due to the fact that XPS is a surface sensitive technique compared to XRD and DR UV-vis methods.

The O1s XP spectrum of bulk $Y_2O_3$—NR sample exhibited two major peaks at 529 eV and 531 eV, which could be assigned to the lattice oxygen in $Y_2O_3$—NR support and $H_2O/OH/O^-$ species on the surface of the support respectively [46]. Existence of high intense peak at 531 eV due to $H_2O/OH/O^-$ species in case of $Y_2O_3$—NR, 1.0Au—$Y_2O_3$NR and 1.5Au—$Y_2O_3$NR samples could be witnessed from the XP spectra. It is clear that intensity of the peak at 529 eV decreased gradually with increase of gold loading, indicating that the composition of surface lattice oxygen species was lowered due to increase in the concentration Y—O—Au species. It is clear that 2.0Au—$Y_2O_3$NR sample showed two peaks at 531 eV and 533 eV. The appearance of XP peak at 533.8 eV could be attributed to interactive (Y—O—Au) species revealing that at high gold loading resulted surface coverage of interactive Y—O—Au species.

Figure 5:
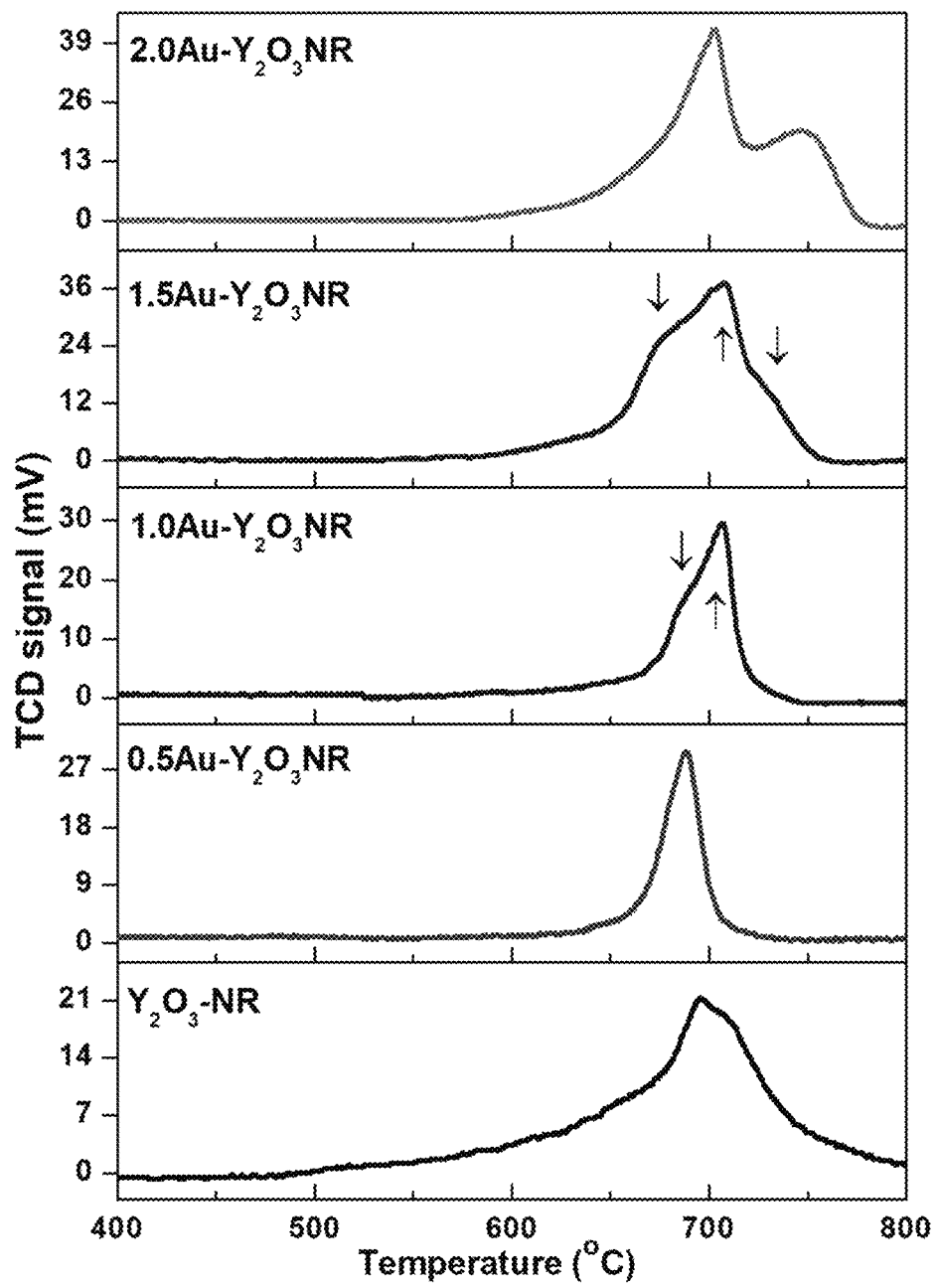
FIG. 5. H$_2$-TPR patterns of gold supported Y$_2$O$_3$ nanorods.

The reducibility of bulk $Y_2O_3$—NR and gold supported $Y_2O_3$—NR samples was investigated using $H_2$-TPR analysis (FIG. 5). The $Y_2O_3$—NR sample reduced in a broad temperature range (500-800° C.) with the reduction peak temperature maximum at 700° C. This observation indicating that $Y_2O_3$—NR is reducible at high temperature. The reduction peak became sharper and the reduction temperature maximum shifted lower (685° C.) after deposition of 0.5 wt % of gold over $Y_2O_3$—NR support indicating the influence of gold on the reducibility of $Y_2O_3$—NR. Presence of low intensity reduction peak indicates that $Y_2O_3$—NR was reduced partially in the temperature range of 500-800° C. It was reported that $H_2$ molecules could react with the oxygen atoms situated over the $Y_2O_3$—NR surface; therefore the reduction temperature and intensity of the $H_2$-TPR peaks could provide the information about the surface oxygen mobility of samples [47].

The $H_2$-TPR pattern of 1.0Au—$Y_2O_3$NR sample exhibited a new reduction peak at 675° C., along with the original reduction peak. An increase in gold content to 1.5 wt % caused appearance of additional reduction peak at 740° C. (total three peaks). Further gold loading to 2.0 wt % lead to form to intense broad peaks centred at 700° C. and 750° C. The observed new reduction peaks displayed substantial broadening and this might be due to random distribution of Au ions on the surface of $Y_2O_3$—NR support. This observation indicates that deposition of Au with $Y_2O_3$ nanorods results in an increase in reducibility of the sample. FIG. 5 clearly indicated that the number and intensity of $H_2$-TPR peaks increased with increase of gold loading; this observation also revealing that the oxygen mobility of the catalyst is increased with increase of gold content from 0.5 to 2.0 wt %. It was also previously reported that the metal oxide catalysts which contained small crystallite size possess a high quantity of mobile oxygen species [48] and also the presence of nanosized gold particles on $Y_2O_3$ nanorods could enhance the surface energy and hence the more active the surface oxygen species.

FT-IR spectra of pyridine adsorbed gold supported $Y_2O_3$—NR samples were obtained to study the acidity of samples. The spectra clearly revealing that the samples showed bands due to pyridine molecules bounded to both Brønsted (B) and Lewis (L) acid sites [49]. Table 2 shows the number of acid sites presented in the synthesized materials. Deposition of gold nanoparticles lowered the number of Brønsted acid sites and increased the quantity of Lewis acid sites. Enhancement in Lewis acid sites is clearly due to the presence of more $Au^0$ nanoparticles on the surface of $Y_2O_3$—NR support. It is well known that material which possesses Brønsted and Lewis acid sites could effectively activate C—H bond in n-alkanes [50]. It is clear from Table 2 that the 1.5Au—$Y_2O_3$—NR sample possessed a large quantity of Lewis acid sites.

TABLE 2

Oxidative cracking of n-propane performance of gold supported $Y_2O_3$-NR catalysts at reaction temperature of 600° C. and GHSV of 48,000h$^{-1}$.

| Catalyst | Number of acid sites | | | Conversion of n-propane (%) | Selectivity of products (%) | | | | |
| --- | --- | --- | --- | --- | --- | --- | --- | --- | --- |
| | Lewis (L) | Brønsted (B) | B/L ratio | | $C_2H_4$ | $C_3H_6$ | $CH_4$ | $C_2H_6$ | $CO_x$ |
| $Y_2O_3$-NR | — | — | — | 26.5 | 16.3 | 38.1 | 4.5 | 6.2 | 34.9 |
| 0.5Au—$Y_2O_3$-NR | 9.4 | 2.3 | 0.244 | 49.6 | 23.4 | 52.5 | 2.2 | 1.9 | 20.4 |
| 1.0Au—$Y_2O_3$-NR | 14.3 | 2.7 | 0.174 | 56.8 | 25.1 | 56.2 | 1.9 | 2.3 | 14.5 |
| 1.5Au—$Y_2O_3$-NR | 19.7 | 3.3 | 0.167 | 75.5 | 26.2 | 64.1 | 1.6 | 1.7 | 6.4 |
| 2.0Au—$Y_2O_3$-NR | 14.5 | 2.8 | 0.197 | 59.5 | 24.3 | 55.8 | 1.8 | 2.2 | 15.9 |

Figure 6A:
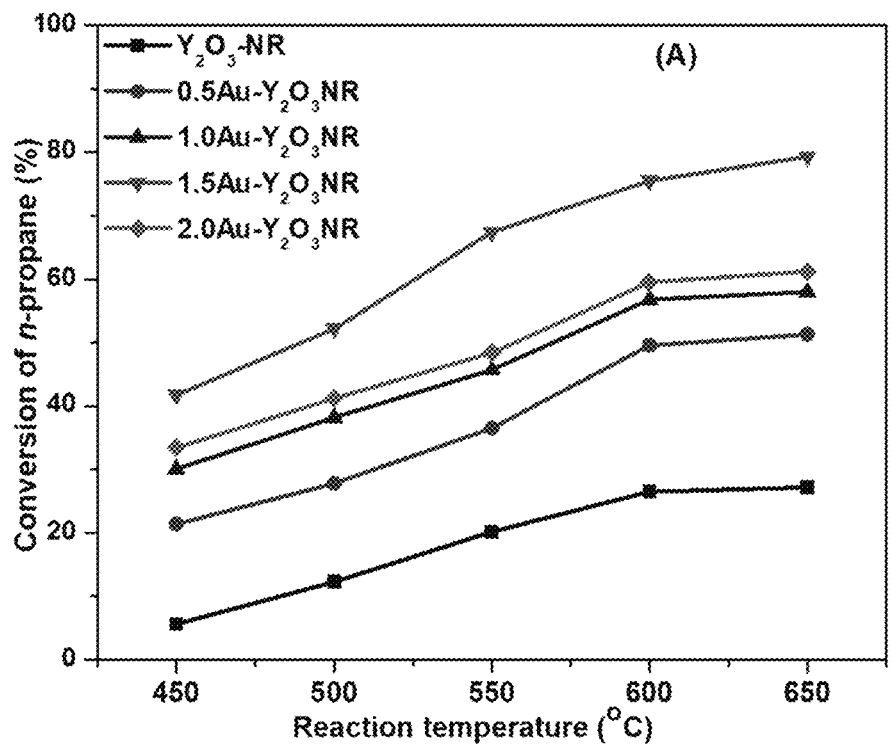
FIGS. 6A-B. Effect of reaction temperature on (A) conversion of n-propane and (B) yield of light olefins, GHSV: 48,000 h$^{-1}$.
Figure 6B:
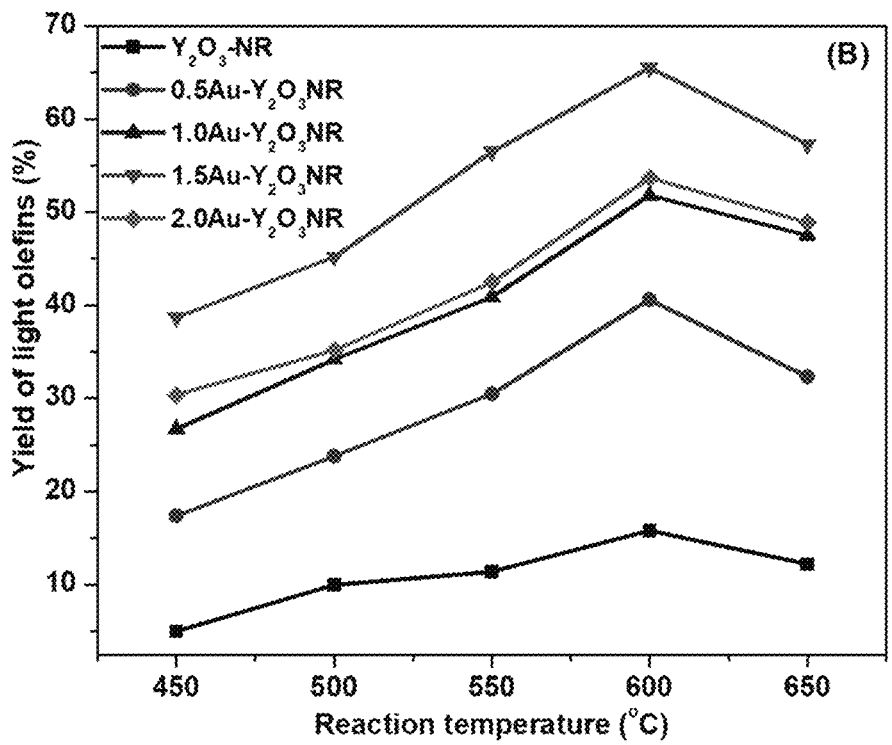

Initially, the influence of the gold loading and reaction temperature on the oxidative cracking activity was investigated (FIG. 6A-B). It is clear from the figure that synthesized $Y_2O_3$—NR sample offered 26.5% n-propane conversion and 15.8% olefins yield at 600° C. The performance of $Y_2O_3$—NR is better than other rare earth metal oxide, $La_2O_3$—NR (22% conversion and 12.4% olefins yield)

under identical reaction conditions. It is possible that liable oxygen species of $Y_2O_3$ could be responsible for its oxidative cracking activity as $Y_2O_3$ is also easily reducible compared with $La_2O_3$. Deposition of 0.5 wt % gold particles over $Y_2O_3$—NR resulted significant enhancement in the catalytic oxidative cracking activity. The n-propane conversion and olefins yield were increased to 49.6% and 40.6% respectively at reaction temperature of 600° C. This observation indicating the positive influence of presence of gold nanoparticles on the surface of $Y_2O_3$—NR. Gradual increase of gold loading to 1.0 wt % and 1.5 wt % resulted gradual increase in both conversion of n-propane and olefins yield at all studied reaction temperatures [FIG. 6, Table 2]. The highest oxidative cracking performance was observed in case of 1.5Au—$Y_2O_3$NR catalyst as it offered 75.5% n-propane conversion and 65.5% olefins yield at 600° C. However, further increase of gold content to 2.0 wt % resulted decline in conversion of n-propane and olefin yield, revealing that presence of large amount of gold particles has an adverse effect and it appears that 1.5 wt % is an optimum loading in case of synthesized $Y_2O_3$—NR support. The reaction temperature also played an important role in performance of gold supported $Y_2O_3$—NR catalysts, the n-propane conversion and olefin yield were increased as the temperature increased from 450° C. to 600° C. in all the catalysts. Gold supported $Ce_{0.5}Zr_{0.5}O_2$ and $La_2O_3$ catalysts also exhibited a similar behavior in oxidative cracking of propane.

It was observed that oxidative cracking performance was improved after gold deposition over the $Y_2O_3$—NR support. It was reported that activation of the C—H bond is the rate limiting step in n-propane oxidative cracking [51]; presence of gold nanoparticles on the surface of $Y_2O_3$—NR is responsible for substantial increase in n-propane conversion and olefins yield. The physico-chemical characterization results indicate that interactions existed between $Y_2O_3$—NR and gold particles. Conversion of n-propane and product distribution at 600° C. in oxidative cracking of n-propane over synthesized catalysts are presented in Table 2. Highest selectivity for $CO_x$ formation (34.9%) was noticed in case of $Y_2O_3$—NR sample. Deposition of gold over $Y_2O_3$—NR support resulted in suppression in $CO_x$ formation. The lowest $CO_x$ selectivity (6.4%) was detected in case of 1.5Au—$Y_2O_3$—NR catalyst. The increase of reaction temperature from 450° C. to 600° C. caused a surge in olefins selectivity (formation of more propylene in all the catalysts), but further raises in reaction temperature to 650° C. led to decrease of olefins selectivity probably due to decomposition of olefins at high temperatures [52].

Figure 7A:
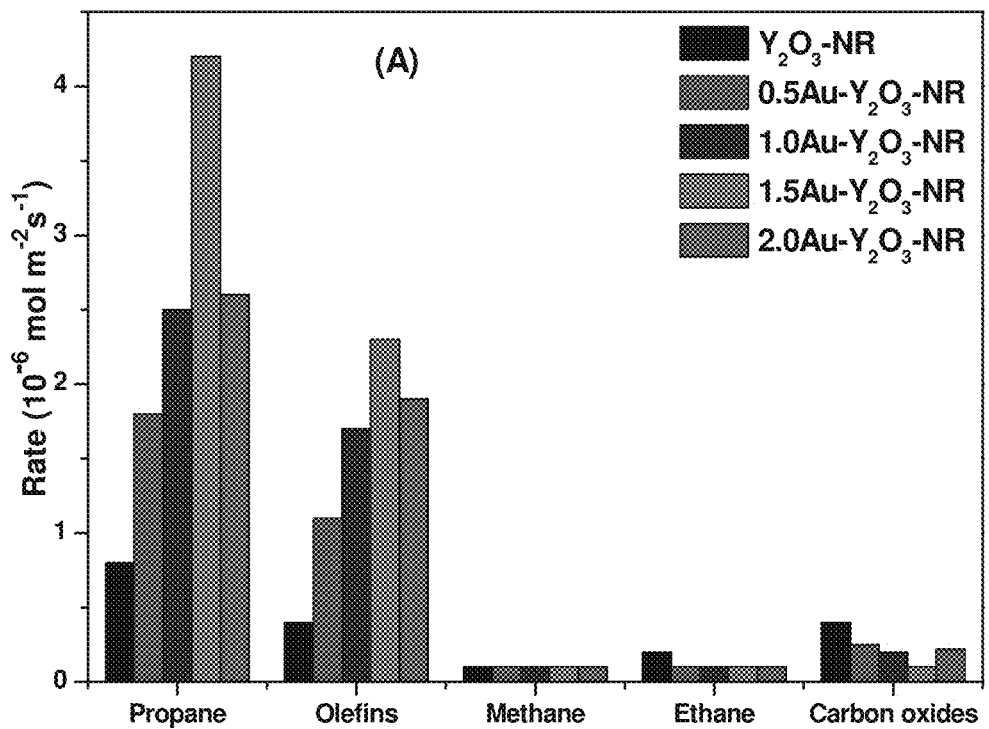
FIGS. 7A-B. (A) Surface normalized reaction rates over synthesized catalysts, (B) correlation between B/L ratio and propylene selectivity (reaction temperature of 600° C. and GHSV of 48,000 h$^{-1}$).
Figure 7B:
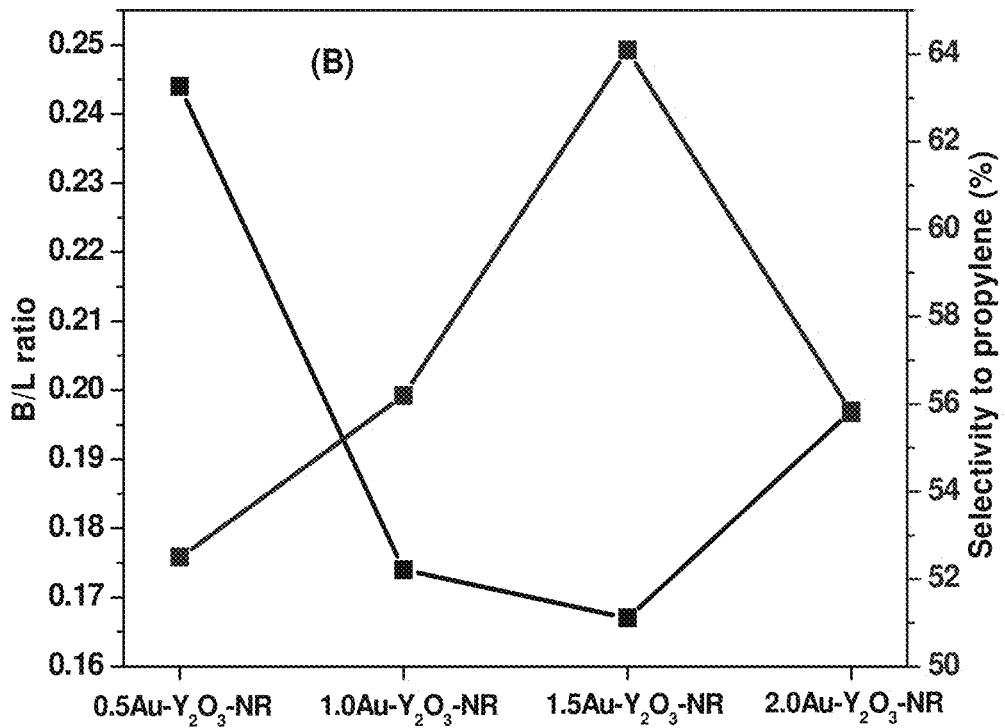

The n-propane conversion and product formation rates were normalized with the total surface area (mol $m^{-2}s^{-1}$) for all synthesized samples (FIG. 7A). Bare $Y_2O_3$—NR sample possessed comparatively large surface area (65 $m^2g^{-1}$); deposition of gold over $Y_2O_3$—NR support resulted in a decrease in surface area (Table 1). However, specific oxidative cracking activity increased almost four fold in case of 1.5Au—$Y_2O_3$—NR sample and thus, propane conversion obtained with gold supported $Y_2O_3$—NR samples was higher than that of bare $Y_2O_3$—NR sample at 600° C. and other studied reaction temperatures. The olefins formation rate increased almost three times for 1.5Au—$Y_2O_3$—NR compared with $Y_2O_3$—NR sample. The high olefins (propylene and ethylene) formation rate observed for 1.5Au—$Y_2O_3$—NR sample could be due to optimum gold loading over $Y_2O_3$—NR support. As the amount of gold loading increases from 0.5 wt % to 1.5 wt %, the B/L ratio decreased due to increase of number of Lewis acid sites. With decrease of B/L ratio, the propylene selectivity was increased. Further increase of gold to 2.0 wt % resulted in a reverse trend (FIG. 7B).

Figure 8:
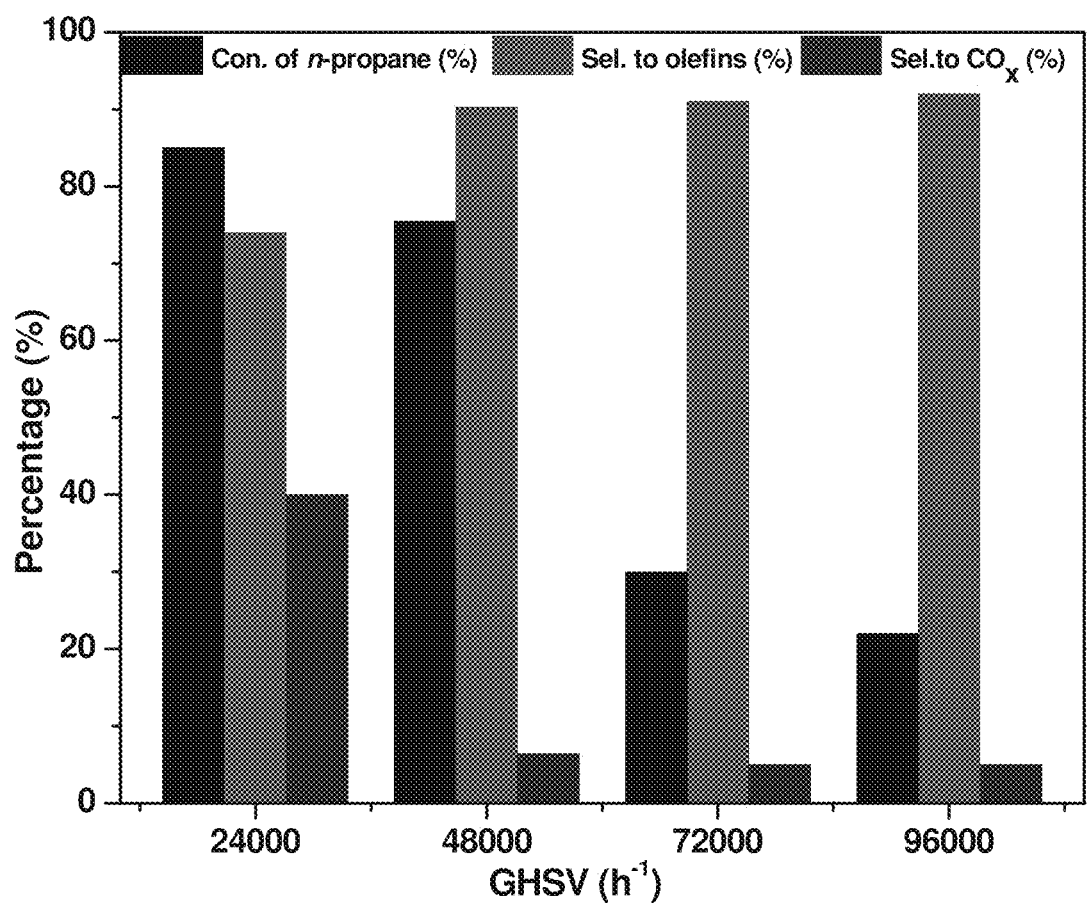
FIG. 8. The influence of GHSV on propane conversion, and olefins & CO$_x$ selectivities over 1.5Au—Y$_2$O$_3$ NR sample (Reaction temperature: 600° C.).
Figure 9A:
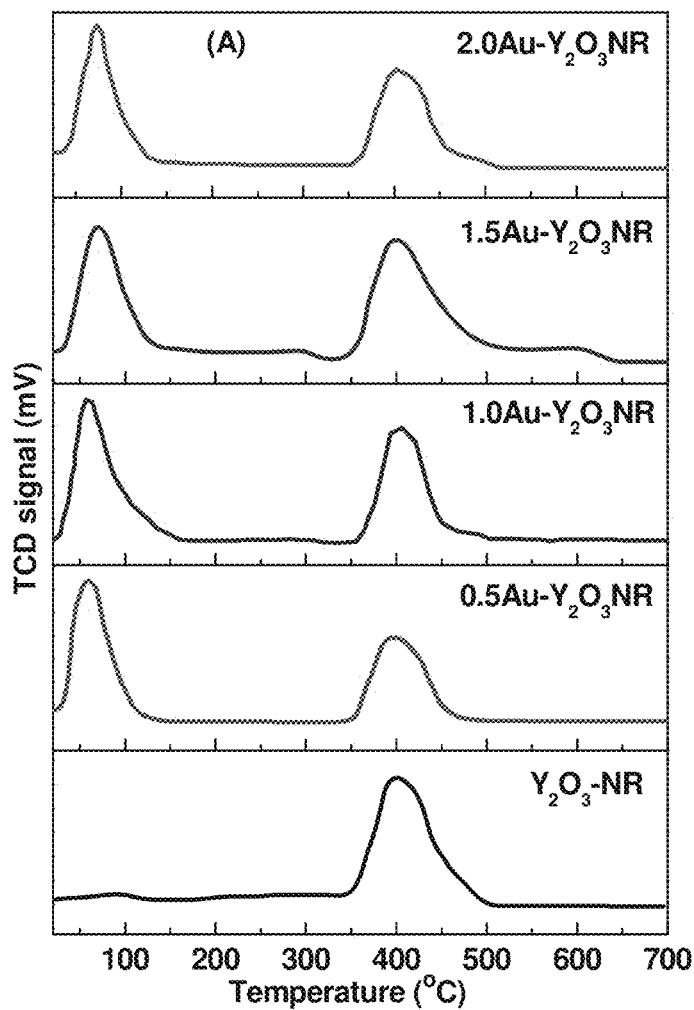
FIGS. 9A-B. (A) The O$_2$-TPD profiles of Y$_2$O$_3$—NR and gold supported Y$_2$O$_3$—NR catalysts, (B) Correlation between O$_2$-TPD peak area and n-propane conversion.

The influence of the gas hourly space velocity (GHSV) over catalytic oxidative cracking performance for synthesized gold supported $Y_2O_3$—NR samples was also studied. FIG. 8 presents n-propane conversion, olefins selectivity and $CO_x$ selectivity observed at different GHSV values in case of 1.5Au—$Y_2O_3$—NR catalyst at 600° C. It is clear that the catalyst offered high n-propane conversion and low olefins selectivity at low GHSV (24000 $h^{-1}$); probably, decomposition of olefins occurred on the catalyst surface due to high residence time. Increase of GHSV value resulted decrease in n-propane conversion, however, the olefins selectivity was increased. Based on the observed results, and in order to obtain the optimum n-propane conversion and selectivity to olefins, GHSV of 48000 $h^{-1}$ was selected for other catalytic tests. To understand the $O_2$ adsorption-desorption capacity of the synthesized catalysts, $O_2$-TPD measurements were performed. The $O_2$-TPD patterns of the $Y_2O_3$—NR and gold supported $Y_2O_3$NR catalysts are displayed in FIG. 9. The bulk $Y_2O_3$—NR sample showed a desorption peak around 405° C., and this peak could be due to chemisorbed oxygen species on the surface of $Y_2O_3$ nanotubes. The gold supported $Y_2O_3$—NR samples exhibited additional $O_2$-TPD peak in the range of 65-75° C., which could be attributed to oxygen species weakly adsorbed on the surface of Au nanoparticles. The area under the $O_2$ desorption peaks was found to be higher in case of 1.5Au—$Y_2O_3$—NR sample compared with other investigated catalysts, suggesting that catalyst had more active oxygen species. It was previously reported that the $O_2$ desorption behavior depends on the quantity and strength of chemisorbed $O_2$ species, which could easily desorb at low temperature [53].

Figure 9B:
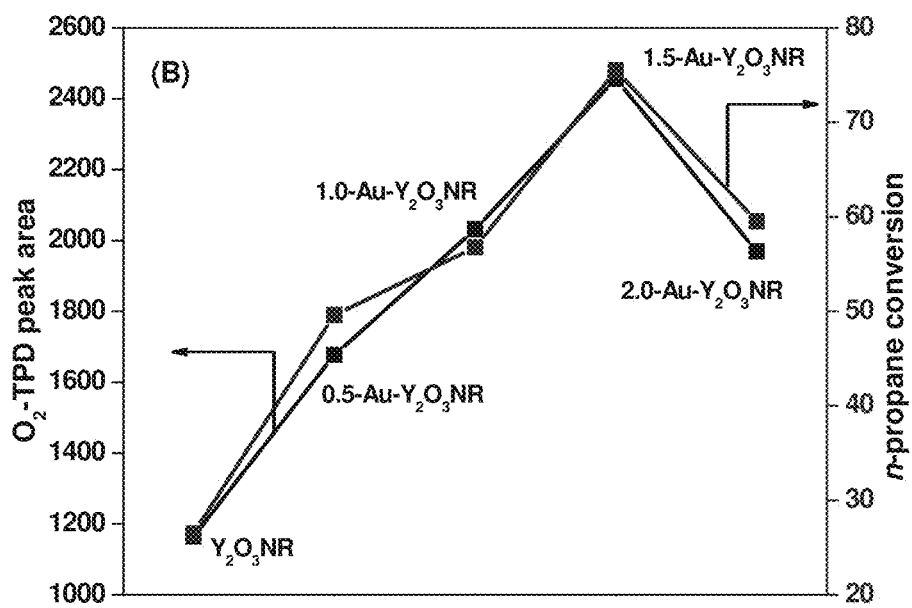

It is known that the oxygen mobility of the catalyst is an important factor in an oxidation reaction given that if the oxygen species presents sufficient mobility, the lattice oxygens can become involved in the catalytic process as well [54]. The oxygen adsorption capacity for each sample was calculated based on the oxygen uptake in the $O_2$-TPD analysis. These values allow us to estimate the total amount of oxygen available in the catalyst. The 1.5Au—$Y_2O_3$NR sample exhibited high $O_2$-TPD peak area indicating that this sample has a high amount of mobile oxygen species, as also indicated by the characterization results discussed previously favoring high catalytic oxidative cracking activity and there is a correlation between $O_2$-TPD peak area and the catalytic activity for the catalysts (FIG. 9B).

To determine TOFs based on Au dispersion, first we determined the gold dispersion using CO chemisorption measurements and then measured the TOF values. It is clear that the Au dispersion is gradually decreased with increase of gold loading from 0.5 wt % to 2.0 wt %. It has been found that n-propane conversion and TOF values has a different trend to Au dispersion as the highest gold dispersion was observed for 0.5Au—$Y_2O_3$NR sample but the highest oxidative cracking activity was observed for 1.5Au—$Y_2O_3$NR sample. Therefore, dispersion of gold particles on the support surface is not a major influencing factor for oxidative cracking ability of synthesized catalysts.

Figure 10A:
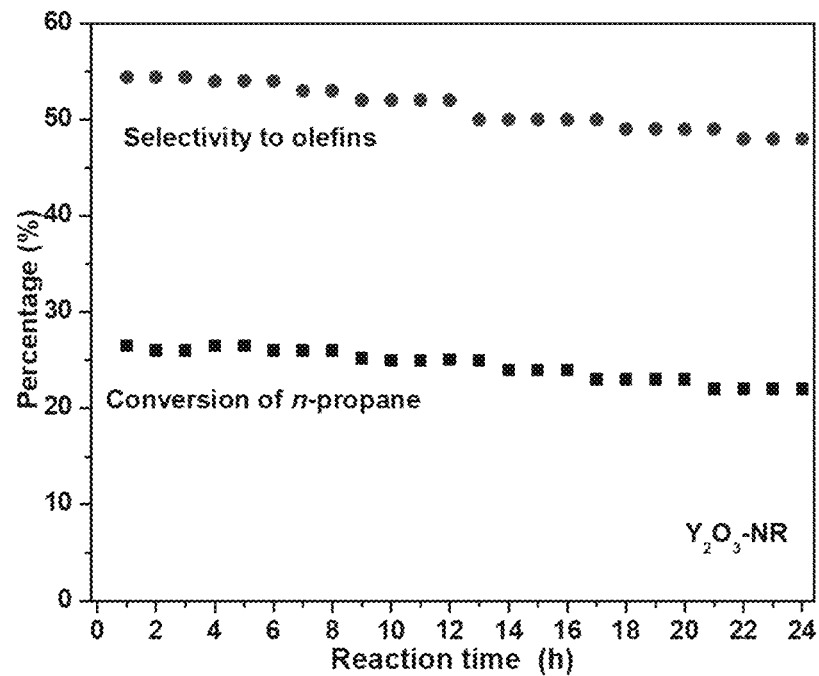
FIGS. 10A-B. Time on stream analysis of (A) Y$_2$O$_3$—NR and (B) 1.5Au—Y$_2$O$_3$—NR catalysts (Reaction temperature: 600° C., GSHV: 48000 h$^{-1}$).
Figure 10B:
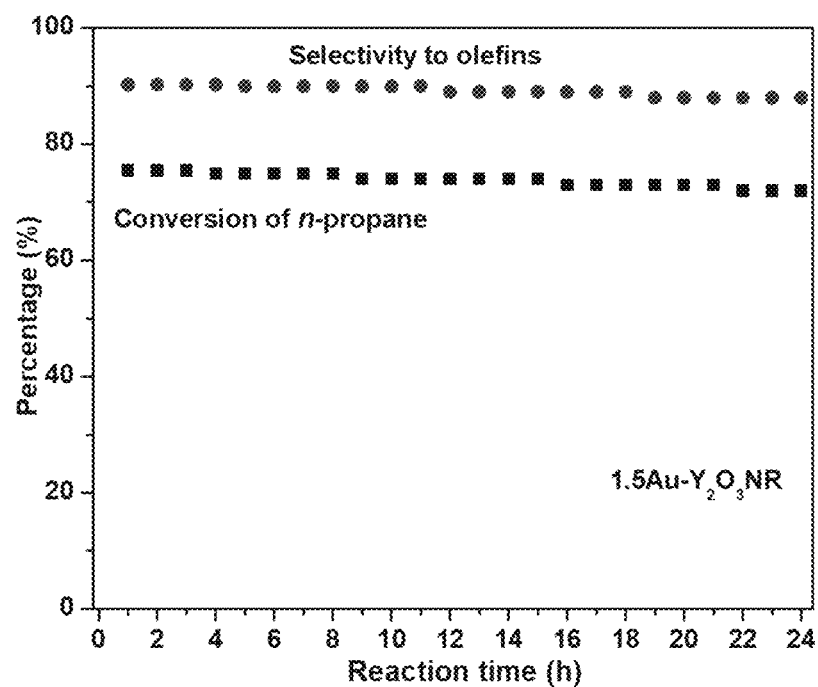

It is known that an increased number of mobile surface oxygen species enhances the rate of oxidation reactions tremendously [55]. It is clear from $H_2$-TPR results that the movement of oxygen species in $Y_2O_3$—NR support is lower than gold supported $Y_2O_3$—NR samples. The observed high catalytic performance of the gold supported $Y_2O_3$—NR catalysts indicate that mobility of the oxygen species of these catalysts could be the key factor. The time on stream analysis for $Y_2O_3$—NR and 1.5Au—$Y_2O_3$—NR samples was performed at a reaction temperature of 600° C. Catalytic oxidative cracking activity of $Y_2O_3$—NR and 1.5Au—$Y_2O_3$—NR samples was tested for 24 hours without any interruption, and activity results are presented in FIG. 10A-B. A minor decrease in n-propane conversion and olefins selectivity levels was observed in case of $Y_2O_3$—NR sample, however 1.5Au—$Y_2O_3$—NR have not exhibited any decreased trend. Considering the fact the reaction environment is substantially different compared to catalyst calcination conditions, as well as that there might be formation of coke during the process, there is a clear possibility for alternations in the structural features of the catalyst samples. To examine the changes, TEM analysis for both fresh and spent 1.5Au—$Y_2O_3$NR catalysts (as a representative sample) was performed. The results suggest that the particle size of gold nanoparticles slightly increased after the reaction. It is possible that agglomeration of gold nanoparticles could be the reason for decreasing activity trend in oxidative cracking.

The observed results clearly indicated that addition of gold significantly enhanced the performance of $Y_2O_3$—NR sample for oxidative cracking of n-propane. It is clear from the characterization results that the total acidity increases with the gold deposition on $Y_2O_3$—NR support, suggesting that Au ions are the additional source of acidity on Au—$Y_2O_3$ NR catalysts. Martins et al [56] reported that catalysts having acidic properties could promote the activation of alkanes through the formation of carbenium intermediates. Accordingly, it is reasonable to argue that the n-propane is protonating to form $C_3H_9^+$, which decomposes into $H_2$ and $C_3H_7^+$ or $CH_4$ and $C_2H_5^+$ on the surface of Au—$Y_2O_3$ catalysts. Propene and ethene are formed after deprotonation of $C_3H_7^+$ and $C_2H_5^+$, respectively. Previously, $V_2O_5/SiO_2$ and Au—$V_2O_5/SiO_2$ catalysts were tested for oxidation of n-propane at 420° C. [57]. The authors observed that addition of gold resulted in an increase in the conversion of n-propane. The same effect was observed when gold was added to Au—$MoO_3/SiO_2$ catalyst. Sa et al [58] reported that the active site is believed to be a combination between cationic gold and a rare earth oxide ($La_2O_3$), which activates the n-butane at low temperatures. The catalyst is selective towards alkene formation and does not provide sites for combustion reactions. The addition of gold also appears to stabilize lanthanum oxycarbonate species that may play a role in enhancing the performance of the gold-promoted oxide catalysts. Our previous studies also revealed a similar observation that deposition of gold enhanced the oxidative cracking ability of $CeO_2$—$ZrO_2$ and $La_2O_3$ supports [21]. Recently, Wang et al [59] used ab initio molecular dynamics simulations and reported that the charge state of the supported Au particle is dynamically changing during the catalytic cycle, where the charging/discharging of Au particle not only controls the amount of $O_2$ adsorbed at the Au particle/oxide interface but also strongly influences the energetics of all the redox steps. Therefore, it is clear that the presence of nanosized gold is helpful to obtain better performance in the catalytic oxidative cracking process.

The physico-chemical characterization results measured from the different techniques are useful to realize the reasons for superior activity of gold supported $Y_2O_3$—NR samples in n-propane oxidative cracking. The FE-SEM results revealed that prepared gold supported $Y_2O_3$—NR samples possessed $Y_2O_3$ naosized rods and gold nanoparticles. It is widely reported that highly dispersed nanosized gold catalysts show superior catalytic performance compared to catalysts with micro-sized particles [60]. It was previously observed that morphology of catalytically active component and support play an important role to obtain superior catalytic performance. The $H_2$-TPR results revealed that gold supported $Y_2O_3$—NR catalysts are more easily reducible than bulk $Y_2O_3$—NR sample and it was also reported in the literature that gold supported $Y_2O_3$ catalysts possessed more oxygen storage capacity than the bulk $Y_2O_3$ material [61]. It is clear that the existence of gold-$Y_2O_3$ interactive species could enhance the redox ability of the catalysts. The characterization results also revealed that gold supported $Y_2O_3$—NR catalysts consisted of small particle size, considerably large specific surface area, large quantity of Lewis acid sites and easy reducibility; the combination of these properties are essentially responsible for the superior catalytic oxidative cracking ability.

Conclusions

A simple alkali assisted hydrothermal method was used to prepare $Y_2O_3$ nanorods sample. The synthesized $Y_2O_3$ nanorods was used as a support to prepare gold (0.5, 1.0, 1.5 and 2.0 wt %) supported $Y_2O_3$ nanorods samples by chemical reduction method. Powder XRD, FT-IR, FE-SEM, DR UV-vis, $N_2$-physisorption, XPS, $H_2$-TPR and $O_2$-TPD techniques were used to characterize the synthesized catalysts. The obtained results indicated the existence of a synergistic effect between gold species and $Y_2O_3$ NR support due to strong metal-support interaction. The synthesized Au—$Y_2O_3$—NR samples were used for oxidative cracking of n-propane to produce light olefins. The bulk $Y_2O_3$ nanorods offered 20% of n-propane conversion and 25% of light olefins (ethylene and propylene) selectivity at 600° C. Deposition of gold nanoparticles over the $Y_2O_3$ nanorods resulted in a significant enhancement in both conversion of n-propane and selectivity to olefins. The 1.5Au—$Y_2O_3$—NR catalyst showed highest activity (75.5% conversion of n-propane and 90.3% olefins selectivity) at 600° C. due to the presence of more Lewis acid sites, mobile oxygen species and also $Au^{\delta+}$—O—Y species in the sample. Time on stream analysis indicated that gold supported $Y_2O_3$ nanorod catalysts exhibited continuous stable activity for 24 h with a slight loss of activity due to agglomeration of gold particles.

Acknowledgements

This project was funded by the research and development office (RDO) at the Ministry of Education, Kingdom of Saudi Arabia: Grant no (HIQI-20-2019). The inventors also acknowledge with thanks research development office (RDO-KAU) at King Abdulaziz University for technical support.

REFERENCES

[1] Bender M. An overview of industrial processes for the production of olefins-C4 hydrocarbons. Chem Bio Eng Rev 2014; 1: 136-147. doi.org/10.1002/cben.201400016.
[2] Louis B, Pereira M, Santos F, Esteves P, Sommer J. Alkane activation over acidic zeolites: The first step. Chem Eur J 2010; 16: 573-576. doi.org/10.1002/chem.200901737.
[3] Corma A, Melo F V, Sauvanaud L, Ortega F. Light cracked naphta processing: Controlling chemistry for maximum propylene production. Catal Today 2005; 107-108: 699-706. doi.org/10.1016/j.cattod.2005.07.109.

[4] Xu B, Sievers C, Hong S B, Prins R, van Bokhoven J A. Catalytic activity of Brønsted acid sites in zeolites: Intrinsic activity, rate-limiting step, and influence of the local structure of the acid sites. J Catal 2006; 244: 163-168. doi.org/10.1016/j.jcat.2006.08.022.

[5] Subramanian R, Panuccio G J, Krummenacher J J, Leeb I C, Schmidt L D. Catalytic partial oxidation of higher hydrocarbons: reactivities and selectivities of mixtures. Chem. Eng Sci 2004; 59: 5501-5507. doi.org/10.1016/j.ces.2004.09.012.

[6] Zhu X, Hofmann J P, Mezari B, Kosinov N, Wu L, Qian Q, Weckhuysen B. M, Asahina S, Ruiz-Martinez J, Hensen E J M. Trimodal, porous hierarchical SSZ-13 zeolite with improved catalytic performance in the methanol-to-olefins reaction. ACS Catal. 2016; 6: 2163-2177. doi.org/10.1021/acscatal.5b02480.

[7] Mol J C. Industrial applications of olefin metathesis. J Mol Catal A 2004; 213: 39-45. doi.org/10.1016/j.molcata.2003.10.049.

[8] Weckhuysen B M, Schoonheydt R A. Alkane dehydrogenation over supported chromium oxide catalysts. Catal Today 1999; 51: 223-232. doi.org/10.1016/50920-5861(99)00047-4.

[9] Zichittella G, Aellen N, Paunović V, Amrute A P, Pérez-Ramirez J. Olefins from natural gas via oxychlorination. Angew Chem Int Ed 2017; 56: 13670-13674. doi.org/10.1002/anie.201706624.

[10] Zichittella G, Stähelin S, Goedicke F M, Pérez-Ramírez J. Selective propylene production via propane oxychlorination on metal phosphate catalysts, ACS Catal. 2019; 9: 5772-5782.

[11] Leveles L, Seshan K, Lercher J A, Lefferts L. Oxidative conversion of propane over lithium-promoted magnesia catalyst: II. Active site characterization and hydrocarbon activation. J Catal 2003; 218: 307-314. doi.org/10.1016/S0021-9517(03)00113-1.

[12] Boyadjian C A, Lefferts L, Seshan K. Catalytic oxidative cracking of hexane as a route to olefins. Appl Catal Gen: A 2010; 372: 167-174. doi.org/10.1016/j.apcata.2009.10.030.

[13] Boyadjian C, Lefferts L. Catalytic oxidative cracking of light alkanes to alkenes. Eur J Inorg Chem 2018; 2018: 1956-1968. doi.org/10.1002/ejic.201701280.

[14] Alonso A, Sherman A M, Wallington T J, Everson M P, Field F R, Roth R, Kirchain R E. Evaluating rare earth element availability: A case with revolutionary demand from clean technologies. Environ Sci Technol 2012; 46: 3406-3414. doi.org/10.1021/es203518d.

[15] Sanchez-Castillo M A, Madon R J, Dumesic J A. Role of rare earth cations in Y zeolite for hydrocarbon cracking. J Phys Chem B 2005; 109: 2164-2175. doi.org/10.1021/jp0489875.

[16] Vogt E T C, Weckhuysen B M. Fluid catalytic cracking: recent developments on the grand old lady of zeolite catalysis, Chem Soc Rev 2015; 44: 7342-7370. doi.org/10.1039/C5CS00376H.

[17] Yoshimura Y, Kijima N, Hayakawa T, Murata K, Suzuki K, Mizukami F, Matano K, Konishi T, Oikawa T, Saito M, Shiojima T, Shiozawa K, Wakui K, Sawada G, Sato K, Matsuo S, Yamaoka N. Catalytic cracking of naphtha to light olefins, Catal Sury Jpn 2000; 4: 157-167. doi.org/10.1023/A:1011463606189.

[18] Nakamura M, Takenaka S, Yamanaka I, Otsuka K. Production of alkenes through oxidative cracking of n-butane over OCM catalysts. Stud Surf Sci Catal 2000; 130: 1781-1786. doi.org/10.1016/S0167-2991(00)80459-0.

[19] Landau M V, Kaliya M L, Herskowitz M, van den Oosterkamp P F, Bocque P S G. Produce light olefins from paraffins by catalytic oxidation, Chemtech 1996; 26: 24-29.

[20] Blay V, Louis B, Miravalles R, Yokoi T, Peccatiello K A, Clough M, Yilmaz B. Engineering zeolites for catalytic cracking to light olefins. ACS Catal 2017; 7: 6542-6566. doi.org/10.1021/acscatal.7b02011.

[21] Narasimharao K, Ali T T. Catalytic oxidative cracking of propane over nanosized gold supported $Ce_{0.5}Zr_{0.5}O_2$ catalysts, Catal Lett 2013; 143: 1074-1084. doi.org/10.1007/s10562-013-1073-8; Al-Sultan F S, Basahel S N, Narasimharao K. Catalytic oxidative cracking of n-propane over nanosized gold supported $La_2O_3$ catalysts. Fuel 2018; 233: 796-804. doi.org/10.1016/j.fuel.2018.06.130.

[22] Dobrosz-Gomez I, Kocemba I, Rynkowski J M. Factors influencing structure and catalytic activity of $Au/Ce_{1-x}Zr_xO_2$ catalysts in CO oxidation. Appl Catal B: Environ. 2009; 88: 83-97. doi.org/10.1016/j.apcatb.2008.09.028.

[23] Emayavaramban P, Babu S G, Karvembu R, Kadirvelu K, Dharmaraj N. Gold nanoparticles supported on magnesium oxide nanorods for oxidation of alcohols. J Nanosci Nanotechnol 2016; 16: 2517-2526. doi.org/10.1166/jnn.2016.10778.

[24] Dimitratos N, Villa A, Prati L, Hammond C, Chan-Thaw C E, Cookson J. Effect of the preparation method of supported Au nanoparticles in the liquid phase oxidation of glycerol. Appl Catal A: Gen 2016; 514: 267-275. doi.org/10.1016/j.apcata.2015.12.031.

[25] Kumar C P, Gaab S, Muller T E, Lercher J A. Oxidative dehydrogenation of light alkanes on supported molten alkali metal chloride catalysts. Topics Catal 2008; 50:156-167. doi.org/10.1007/s11244-008-9102-3.

[26] Hutchings G J, Taylor S H. Designing oxidation catalysts, Catal Today 1999; 49: 105-113. doi.org/10.1016/S0920-5861(98)00414-3.

[27] Fokema M D, Ying J Y. The selective catalytic reduction of nitric oxide with methane over scandium oxide, yttrium oxide and lanthanum oxide. Appl Catal B: Environ. 1998; 18: 71-78. doi.org/10.1016/S0926-3373(98)00025-3.

[28] Guzman J, Corma A. Nanocrystalline and mesostructured $Y_2O_3$ as supports for gold catalysts. Chem Commun 2005; 743-745. doi.org/10.1039/B413338B.

[29] Hajizadeh-Oghaz M, Razavi R S, M. Barekat, M. Naderi, S. Malekzadeh, M. Rezazadeh, Synthesis and characterization of $Y_2O_3$ nanoparticles by sol-gel process for transparent ceramics applications. J Sol-Gel Sci Technol 2016; 78: 682-691. doi.org/10.1007/s10971-016-3986-3.

[30] Al-Sultan F S, Basahel S N, Narasimharao K. Yttrium oxide supported $La_2O_3$ nanomaterials for catalytic oxidative cracking of n-propane to olefins. Catal Lett 2020; 150: 185-195. doi.org/10.1007/s10562-019-02927-z.

[31] Alshehri A A, Narasimharao K. Low temperature oxidation of carbon monoxide over mesoporous $Au—Fe_2O_3$ catalysts. J Nanomaterials, 2017, e8707289. doi.org/10.1155/2017/8707289.

[32] Saravanan T, Anandan P, Azhagurajan M, Arivanandhan M, Pazhanivel K, Hayakawa Y, Jayavel R. Synthesis and characterization of $Y_2O_3$-reduced graphene oxide nanocomposites for photocatalytic applications. Mater Res Express 2016; 3: 075502. doi.org/10.1088/2053-1591/3/7/075502.

[33] Padmalaya G, Sreeja B S, Radha S, Manikandan E, Rajkumar G. Synthesis and characterization of novel chitosan/yttrium oxide nanorods and their electrochemical sensing performance towards Cd (II) ions. J Elec Materi 2019; 48: 3261-3269. doi.org/10.1007/s11664-019-07063-3.

[34] Ismail A A. Synthesis and characterization of $Y_2O_3$/$Fe_2O_3$/$TiO_2$ nanoparticles by sol-gel method. Appl Cat B: Environ. 2005; 58: 115-121. doi.org/10.1016/j.apcatb.2004.11.022.

[35] Qin X, Zhou G, Yang H, Yang Y, Zhang J, Wang S. Synthesis and upconversion luminescence of monodispersed, submicron-sized $Er^{3+}$:$Y_2O_3$ spherical phosphors, J Alloys Compd 2010; 493: 672-677. doi.org/10.1016/j.jallcom.2009.12.188.

[36] Aghazadeh M, Ghaemi M, Golikand A N, Yousefi T, Jangju E. Yttrium oxide nanoparticles prepared by heat treatment of cathodically grown yttrium hydroxide, ISRN Ceramics. 2011, e 542104. doi.org/10.5402/2011/542104.

[37] Nyquist R A, Kagel R O. Handbook of infrared and Raman spectra of inorganic compound and organic Salts. vol. 4, Academic press, Tokyo, Japan, 1997.

[38] Xu J Q, Xiong S J, Wu X L, Li T H, Shen J C, Chu P K. Investigation of activated oxygen molecules on the surface of $Y_2O_3$ nanocrystals by Raman scattering. J Appl Phys 2013; 114: 093512. doi.org/10.1063/1.4820465.

[39] Sharma V, Park K, Srinivasarao M. Colloidal dispersion of gold nanorods: historical background, optical properties, seed-mediated synthesis, shape separation and self-assembly. Mat Sci Eng R 2009; 65: 1-38. doi.org/10.1016/j.mser.2009.02.002.

[40] Khalfaoui M, Knani S, Hachicha M A, Lamine A B. New theoretical expressions for the five adsorption type isotherms classified by BET based on statistical physics treatment. J Colloid Inter Sci 2003; 263: 350-356. doi.org/10.1016/S0021-9797(03)00139-5

[41] Mongstad T, Platzer-Björkman C, Maehlen J P, Mooij L P A, Pivak Y, Dam B, Marstein E S, Hauback B C, Karazhanov S Z. A new thin film photochromic material: oxygen-containing yttrium hydride. Sol Energy Mater Sol Cells 2011; 95: 3596-3599. doi.org/10.1016/j.solmat.2011.08.018.

[42] Gougousi T, Chen Z. Deposition of yttrium oxide thin films in supercritical carbon dioxide, Thin Solid Films 2008; 516: 6197-6204. doi.org/10.1016/j.tsf.2007.11.104.

[43] Cuenya B R, Baeck S H, Jaramillo T F, McFarland E W. Size- and support-dependent electronic and catalytic properties of $Au^0$/$Au^{3+}$ nanoparticles synthesized from block copolymer micelles. J Am Chem Soc 2003; 125: 12928-12934. doi.org/10.1021/ja036468u.

[44] Kruse N, Chenakin S. XPS characterization of Au/$TiO_2$ catalysts: Binding energy assessment and irradiation effects, Appl Catal A: Gen. 2011; 391: 367-376. doi.org/10.1016/j.apcata.2010.05.039.

[45] Weiher N, Bus E, Delannoy L, Louis C, Ramaker D E, Miller J T, van Bokhoven J A. Structure and oxidation state of gold on different supports under various CO oxidation conditions. J Catal 2006; 240: 100-107. doi.org/10.1016/j.jcat.2006.03.010.

[46] Moulder J F, Stickle W F, Sobol P W, Bomben K D. Handbook of X-ray Photoelectron Spectroscopy, Perkin-Elmer, Eden Prairie, Minn., 1992.

[47] Chen D, He D, Lu J, Zhong L, Liu F, Liu J, Yu J, Wan G, He S, Luo Y. Investigation of the role of surface lattice oxygen and bulk lattice oxygen migration of cerium-based oxygen carriers: XPS and designed $H_2$-TPR characterization. Appl Catal B: Environ. 2017; 218: 249-259. doi.org/10.1016/j.apcatb.2017.06.053.

[48] Jaipal M, Chatterjee A. Relative occurrence of oxygen-vacancy pairs in yttrium-containing environments of $Y_2O_3$-doped $ZrO_2$ can be crucial to ionic conductivity. J Phys Chem C 2017; 121: 14534-14543. doi.org/10.1021/acs.jpcc.7b05329.

[49] Hemmann F, Agirrezabal-Telleria I, Jaeger C, Kemnitz E. Quantification of acidic sites of nanoscopic hydroxylated magnesium fluorides by FTIR and $^{15}N$ MAS NMR spectroscopy, RSC Adv. 2015; 5: 89659-89668. doi.org/10.1039/C5RA15116C.

[50] Almutairi S M T, Mezari B, Filonenko G, Magusin P C M M, Pidko E A, Hensen E J M. Influence of extra framework aluminum on the Brønsted acidity and catalytic reactivity of faujasite zeolite. ChemCatChem 2013; 5: 452-466. doi.org/10.1002/cctc.201200612.

[51] Burch R, Hayes M J, C—H bond activation in hydrocarbon oxidation on solid catalysts. J Mol Catal A: Chem 1995; 100: 13-33. doi.org/10.1016/1381-1169(95)00133-6.

[52] Wu N, Zong Z-M, Fei Y-W, Ma J, Guo F. Thermal oxidation stability of poly-α-olefin lubricating oil. Asia-Pac J Chem Eng 2017; 12: 813-817. doi.org/10.1002/apj.2121.

[53] Gavril D, Georgaka A, Karaiskakis G. Kinetic study of oxygen adsorption over nanosized Au/γ-$Al_2O_3$ supported catalysts under selective CO oxidation conditions. Molecules 2012; 17: 4878-4895. doi.org/10.3390/molecules17054878.

[54] Xue L, Zhang C, He H, Teraoka Y. Catalytic decomposition of $N_2O$ over $CeO_2$ promoted $Co_3O_4$ spinel catalyst. Appl Catal B: Environ 2007; 75: 167-174. doi.org/10.1016/j.apcatb.2007.04.013.

[55] Xu H, Li W, Shang S, Yan C. Influence of MgO contents on silica supported nano-size gold catalyst for carbon monoxide total oxidation. J Nat Gas Chem 2011; 20: 498-502. doi.org/10.1016/S1003-9953 (10)60219-8.

[56] Martins R L, Schmal L. Methane activation on super-acidic catalysts based on oxoanion modified zirconium oxide. Appl Catal: A: Gen 2006; 308: 143-152. doi.org/10.1016/j.apcata.2006.04.018.

[57] Ruszel M, Grzybowska B, Gąsior M, Samson K, Gressel I, Stoch J. Effect of Au in $V_2O_5$/$SiO_2$ and $MoO_3$/$SiO_2$ catalysts on physicochemical and catalytic properties in oxidation of $C_3$ hydrocarbons and of CO. Catal Today 2005; 99: 151-19. doi.org/10.1016/j.cattod.2004.09.035.

[58] Sa J, Ace M, Delgado J J, Goguet A, Hardacre C, Morgan K. Activation of Alkanes by Gold-Modified Lanthanum Oxide. ChemCatChem 2011; 3: 394-398. doi.org/10.1002/cctc.201000285.

[59] Wang Y-G, Mei D, Glezakou V-A, Li J, Rousseau R. Dynamic formation of single-atom catalytic active sites on ceria-supported gold nanoparticles. Nat Commun 2015; 6: e6511. doi.org/10.1038/ncomms7511.

[60] Gao Y, Zhang L, van Hoof A J F, Friedrich H, Hensen E J M. A robust Au/$ZnCr_2O_4$ catalyst with highly dispersed gold nanoparticles for gas-phase selective oxidation of cyclohexanol to cyclohexanone. ACS Catal 2019; 9: 11104-11115. doi.org/10.1021/acscatal.9b02821.

[61] Sreethawong T, Sitthiwechvij it N, Rattanachatchai A, Ouraipryvan P, Schwank J W, Chavadej S. Preparation of Au/$Y_2O_3$ and Au/NiO catalysts by co-precipitation and their oxidation activities. Mater Chem Phy 2011; 126: 212-219. doi.org/10.1016/j.matchemphys.2010.11.037.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A catalyst, comprising:
nanorods consisting of $Y_2O_3$; and
gold nanoparticles dispersed on a surface of the nanorods, wherein the gold is present at a concentration of 0.5-2 wt %.

2. The catalyst of claim 1, wherein the $Y_2O_3$ nanorods have a diameter ranging from 10-20 nm.

3. The catalyst of claim 1, wherein the $Y_2O_3$ nanorods have a length ranging from 75-110 nm.

4. The catalyst of claim 1, wherein the gold nanoparticles are spherical in shape.

5. The catalyst of claim 4, wherein the gold nanoparticles have a diameter ranging from 20-50 nm.

6. A method of forming olefins by oxidative cracking, comprising:
reacting an alkane with a reactant gas mixture in the presence of a catalyst according to claim 1 under conditions suitable for forming olefins.

7. The method of claim 6, wherein the alkane is n-propane and the olefins comprise ethylene and propylene.

8. The method of claim 6, wherein the reactant gas mixture comprises oxygen and argon.

9. The method of claim 8, wherein the reactant gas mixture comprises 15-25% oxygen and 75-85% argon.

10. The method of claim 6, wherein the reaction is performed at a temperature of 450° C. to 650° C.

11. The method of claim 6, wherein the reaction occurs under a gas hourly space velocity (GHSV) of 47000-49000 $h^{-1}$.

12. The method of claim 6, wherein at least 75% of the alkane is converted in the reaction.

13. The method of claim 6, wherein the reaction has olefins selectivity of at least 90%.

* * * * *